(12) United States Patent
Wadman

(10) Patent No.: US 8,729,031 B2
(45) Date of Patent: May 20, 2014

(54) COMPOUNDS

(75) Inventor: Sjoerd Nicolaas Wadman, Hertfordshire (GB)

(73) Assignee: Novacta Biosystems Limited, Hertfordshire (GB)

( * ) Notice: Subject to any disclaimer, the term of this patent is extended or adjusted under 35 U.S.C. 154(b) by 152 days.

(21) Appl. No.: 13/147,805

(22) PCT Filed: Feb. 2, 2010

(86) PCT No.: PCT/GB2010/000188
§ 371 (c)(1),
(2), (4) Date: Aug. 4, 2011

(87) PCT Pub. No.: WO2010/089544
PCT Pub. Date: Aug. 12, 2010

(65) Prior Publication Data
US 2011/0294723 A1 Dec. 1, 2011

Related U.S. Application Data

(60) Provisional application No. 61/149,857, filed on Feb. 4, 2009.

(51) Int. Cl.
*C07K 7/54* (2006.01)
*A61K 38/04* (2006.01)
*A61K 38/12* (2006.01)
*A61K 38/10* (2006.01)
*A61K 38/00* (2006.01)
*C07K 7/08* (2006.01)
*C07K 16/18* (2006.01)
*A61K 38/16* (2006.01)
*A61K 39/395* (2006.01)

(52) U.S. Cl.
CPC . *C07K 7/54* (2013.01); *A61K 38/04* (2013.01); *A61K 38/12* (2013.01); *A61K 38/10* (2013.01); *A61K 38/00* (2013.01); *A61K 38/164* (2013.01); *A61K 39/39533* (2013.01); *C07K 7/08* (2013.01); *C07K 16/18* (2013.01)
USPC ............. 514/21.4; 514/2.4; 514/2.7; 514/2.3; 514/1.1; 514/21.1; 514/2.9; 530/300; 530/317; 530/326

(58) Field of Classification Search
CPC ............ C07K 7/54; C07K 7/08; C07K 16/18; A61K 38/12; A61K 38/10; A61K 38/00; A61K 38/164; A61K 38/04; A61K 39/39533
USPC ........... 514/21.4, 2.4, 2.7, 2.9, 1.1, 21.1, 2.3; 530/326, 300, 317
See application file for complete search history.

(56) References Cited

U.S. PATENT DOCUMENTS

| | | |
|---|---|---|
| 3,710,795 A | 1/1973 | Higuchi et al. |
| 5,112,806 A | 5/1992 | Chatterjee et al. |
| 5,304,540 A | 4/1994 | Blackburn et al. |
| 5,667,991 A | 9/1997 | Koller et al. |
| 5,683,675 A | 11/1997 | Vedia et al. |
| 5,763,395 A | 6/1998 | Blackburn et al. |
| 5,958,873 A | 9/1999 | Sakr et al. |
| 5,985,823 A | 11/1999 | Goldstein |
| 6,022,851 A | 2/2000 | Vertesy et al. |
| 6,569,830 B1 | 5/2003 | Climo et al. |
| 7,122,514 B2 | 10/2006 | Climo et al. |
| 7,989,416 B2 | 8/2011 | Boakes et al. |
| 8,329,644 B2 * | 12/2012 | Wadman ........................ 514/2.2 |
| 2009/0203583 A1 | 8/2009 | Wadman et al. |
| 2010/0048459 A1 | 2/2010 | Boakes et al. |
| 2010/0168410 A1 | 7/2010 | Cade et al. |
| 2010/0179207 A1 | 7/2010 | Wadman |
| 2010/0261638 A1 | 10/2010 | Wadman |

FOREIGN PATENT DOCUMENTS

| | | |
|---|---|---|
| DE | 197 45 583 | 4/1999 |
| EP | 0195358 | 9/1986 |
| EP | 0195359 | 9/1986 |
| EP | 0572942 | 12/1993 |

(Continued)

OTHER PUBLICATIONS

International Search Report and Written Opinion in PCT/GB2010/000188 mailed May 20, 2010.
International Preliminary Report in PCT/BB2010/000188 mailed Apr. 19, 2011.
Arioli et al. "Gardimycin, a new antibiotic from *Actinoplanes*: III. Biological properties" The Journal of Antibiotics 29(5):511-515 (1976).
Berge et al. "Pharmaceutical salts" Journal of Pharmaceutical Sciences 66(1):1-19 (1977).
Bierbaum et al. "Cloning, sequencing and production of the lantibiotic mersacidin" FEMS Microbiology Letters 127:121-126 (1995).

(Continued)

*Primary Examiner* — Julie Ha
(74) *Attorney, Agent, or Firm* — Morgan, Lewis & Bockius LLP

(57) ABSTRACT

Compounds of formula (IV) and pharmaceutical compositions comprising the same are described, wherein X1 and X2, $R^3$, L, $Ar^1$, p and Z have the values disclosed herein.

(IV)

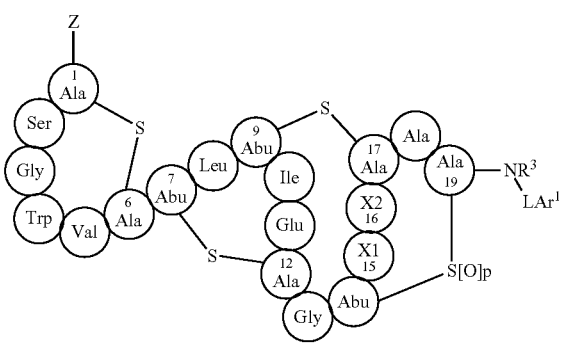

26 Claims, 6 Drawing Sheets

(56) References Cited

FOREIGN PATENT DOCUMENTS

| | | |
|---|---|---|
| EP | 0700998 | 3/1996 |
| EP | 1646646 | 3/2007 |
| WO | WO 91/07949 | 6/1991 |
| WO | WO 91/11172 | 8/1991 |
| WO | WO 94/02518 | 2/1994 |
| WO | WO 97/00694 | 1/1997 |
| WO | WO 98/55148 | 12/1998 |
| WO | WO 02/00196 | 1/2002 |
| WO | WO 02/088367 | 11/2002 |
| WO | WO 02/103010 | 12/2002 |
| WO | WO 03/099862 | 12/2003 |
| WO | WO 2004/033706 | 4/2004 |
| WO | WO 2005/093069 | 10/2005 |
| WO | WO 2006/080920 | 8/2006 |
| WO | WO 2007/036706 | 4/2007 |
| WO | WO 2007/083112 | 7/2007 |
| WO | WO 2008/151434 | 12/2008 |
| WO | WO 2009/010763 | 1/2009 |
| WO | WO 2009/010765 | 1/2009 |
| WO | WO 2010/058238 | 5/2010 |
| WO | WO 2010/082018 | 7/2010 |
| WO | WO 2010/082019 | 7/2010 |
| WO | WO 2010/092019 | 7/2010 |
| WO | WO 2010/089544 | 8/2010 |

OTHER PUBLICATIONS

Bierman et al. "Plasmid cloning vectors for the conjugal transfer of DNA from *Escherichia coli* to *Streptomyces* spp." Gene 116(1): 43-49 (1992).

Britton et al. "Genome-Wide Analysis of the Stationary-Phase Sigma Factor (Sigma-H) Regulon of *Bacillus subtilis*" Journal of Bacteriology 184(17):4881-4890 (2002).

Castiglione et al. "A novel lantibiotic acting on bacterial cell wall synthesis produced by uncommon actinomycete *Planomonospora* sp." Biochemistry 46:5884-5895 (2007).

Chatterjee et al. "Biosynthesis and Mode of Action of Lantibiotics" Chem. Rev. 105:633-683 (2005).

Coronelli et al. "Gardimycin, A New Antibiotic From Actinoplanes: II. Isolation and preliminary characterization" Journal of Antibiotics 29(5):507-510 (1976).

Cotter et al. "Bacterial lantibiotics: strategies to improve therapeutic potential" Current Protein Peptide Science 6(1):61-75 (2005).

Dabard et al. "Ruminococin A, a new lantibiotic produced by a *Ruminococcus gnavus* strain isolated from human feces" Appl. Environ. Microbiol. 67:4111-4118 (2001).

Dawson "Lantibiotics as antimicrobial agents" Expert Opinion on Therapeutic Patents, Informa Healthcare, GB, 17(4):365-369 (2007).

Dower et al. "High efficiency transformation of *E. coli* by high voltage electroporation" Nucleic Acids Research 16(13):6127-6145 (1988).

Fleisher et al. "Improved oral drug delivery: solubility limitations overcome by the use of prodrugs" Advanced Drug Delivery Reviews 19(2):115-130 (1996).

Flett et al. "High efficiency intergeneric conjugal transfer of plasmid DNA from *Escherichia coli* to methyl DNA-restricting *Streptomycetes*" FEMS Microbiology Letters 155(2): 223-229 (1997).

Fukase et al. "Synthase study of peptide antibiotic nisin. V. Total synthesis of nisin" Bull. Chem. Soc. Jpn. 65:2227-2240 (1992).

Fumi et al. "Rifaximin treatment for symptoms of irritable bowel syndrome" The Annals of Pharmacotherapy 42:408-412 (2008).

Gardiner et al. "Fate of the Two-Component Lantibiotic Lacticin 3147 in the Gastrointestinal Tract" Applied and Environmental Microbiology 73(21):7103-7109 (2007).

Gravesen et al. "pbp2229-Mediated nisin resistance mechanism in *Listeria monocytogenes* confers cross-protection to class IIa bacteriocins and affects virulence gene expression" Applied and Environmental Microbiology 70(3): 1669-1679 (2004).

Guder et al. "Role of the single regulator MrsR1 and the two-component system MrsR2/K2 in the regulation of mersacidin production and immunity" Applied and Environmental Microbiology 68(1):106-113 (2002).

Guiotto et al. "PEGylation of the antimicrobial peptide nisin A: problems and perspectives" Il Farmaco 58(1):45-50 (2003).

Gust et al. "PCT-targeted *Streptomyces* gene replacement identifies a protein domain needed for biosynthesis of the sesquiterpene soil odor geosmin" PNAS 100(4): 1541-1546 (2003).

Gust et al. "λRed-mediated genetic manipulation of antibiotic-producing *Streptomyces*" Advances in Applied Microbiology 54:107-128 (2004).

Heinzelmann et al. "A glutamate mutase is involved in the biosynthesis of the lipopeptide antibiotic friulimicin in *Actinoplanes friuliensis*" Antimicrobial Agents and Chemotherapy 47(2): 447-457 (2003).

Hilger et al. "Differential binding of IgG and IgA antibodies to antigenic determinatns of bovine serum albumin" Clin. Exp. Immunol. 123:387-394 (2001).

Holtsmark, et al. "Purification, Characterization, and Gene Sequence of Michiganin A, an Actagardine-Like Lantibiotic Produced by the Tomato Pathogen *Clavibacter michiganesis* subsp. *michiganensis*" Applied and Environmental Microbiology 72(9):5814-5821 (2006).

Kettenring et al. "Sequence determination of actagardine, a novel lantibiotic, by homonuclear 2D NMR spectroscopy" J. Antibiot. 43(9):1082-1088 (1990).

Lonetto et al. "The sigma 70 family: sequence conservation and evolutionary relationships" Journal of Bacteriology 174(12): 3843-3849 (1992).

Louie et al. "A phase 2 study of the toxin binding polymer tolevamer in patients with *C. difficile* associated diarrhoea" Proceedings of the 14th European Congress of Clinical Microbiology and Infectious Diseases, Prague Congress Centre, Prague, Czech Republic, P548 (May 1-4, 2004).

Louie et al. "Tolemaver (GT160-246) binds *Clostridium* cytotoxins A/B and is associated with restoration of components of the anaerobic intestinal microflora during treatment of *C. difficile* associated diarrhoea" Proceedings of the 14th European Congress of Clinical Microbiology and Infectious Diseases, Prague Congress Centre, Prague, Czech Republic, P855 (May 1-4, 2004).

Malabarba et al. "Physico-chemical and biological properties of actagardine and some acid hydrolysis products" The Journal of Antibiotics 38(11):1506-1511 (1985).

Malabarba et al. "Synthesis and biological activity of some amide derivatives of the lantibiotic actagardine" The Journal of Antibiotics 43(9):1089-1097 (1990).

Marahiel et al. "Regulation of peptide antibiotic production in *Bacillus*" Molecular Microbiology 7(5):631-636 (1993).

McClerren et al. "Discovery and in vitro biosynthesis of haloduracin, a two-component lantibiotic" PNAS 103(46):17243-17248 (2006).

Miner et al. "Steroid-refractory ulcerative colitis treated with corticosteroids, metronidazole and vancomycin: a case report" BMC Gastroenterology 5:3 (2005).

O'Sullivan et al. "High- and low-copy-number *Lactococcus* shuttle cloning vectors with features for clone screening" Gene 137:227-231 (1993).

Parenti et al. "Gardimycin, a new antibiotic from Actinoplanes. I. Description of the producer strain and fermentation studies" The Journal of Antibiotics 29(5):501-506 (1976).

Rea et al. "Antimicrobial activity of lacticin 3147 against *Clostridium difficile* strains" Journal of Medical Microbiology 56:940-946 (2007).

Rey et al. "Complete genome sequence of the industrial bacterium *Bacillus licheniformis* and comparisons with closely related *Bacillus* species" Genome Biology 5(10):R77 (2004).

Sahl et al. "Lantibiotics: Biosynthesis and biological activities of uniquely modified peptides from gram-positive bacteria" Ann. Rev. Microbiology 52:41-79 (1998).

Somma et al. "Gardimycin, a new antibiotic inhibiting peptidoglycan synthesis" Antimicrobial Agents and Chemotherapy 11(3):396-401 (1977).

Szekat et al. "Construction of an expression system for site-directed mutagenesis of the lantibiotic mersacidin" Applied and Environmental Microbiology 69(7):3777-3783 (2003).

"Treatment of *Clostridium difficile*—Associated Disease (CDAD)" Obstetrics and Gynecology 109(4):993-995 (2007).

(56) References Cited

OTHER PUBLICATIONS

Turner et al. "Solution structure of plantaricin C, a novel lantibiotic" Eur. J. Biochem. 264:833-839 (1999).
Turtell et al. "The use of nisin in cheesemaking. Chapter 5: International acceptance of nisin as a food preservative" Bulletin of the Int. Dairy Fed. 329:20-23 (1988).
Ugurlu et al. "Colonic delivery of compression coated nisin tablets using pectin/HPMC polymer mixture" Eur. J. Pharm. Biopharm. 67:202-210 (2007).
van Kraaij et al. "Lantibiotics: biosynthesis, mode of action and applications" Nat. Prod. Rep. 16:575-587 (1999).
Zimmermann et al. "The three-dimensional solution structure of the lantibiotic murein-biosynthesis-inhibitor actagardine determined by NMR" Eur. J. Biochem. 246:809-819 (1997).
Altena, Karsten, et al., "Biosynthesis of the lantibiotic mersacidin: organization of a type B lantibiotic gene cluster," Applied and Environmental Microbiology, Jun. 2000, pp. 2565-2571, vol. 66, No. 6.
Zimmerman, Norbert, et al., "The tetracyciic lantibiotic actagardine H-NMR and C-NMR assignments and revised primary structure," European Journal of Biochemistry, Mar. 15, 1995, pp. 786-797, vol. 228, No. 3.
Vertesy, Laszlo, et al., "Ala(0)-actagardine, a new lantibiotic from cultures of *Actinoplanes liguriae* ATCC 31048," Journal of Antibiotics, Japan Antibiotics Research Association, Aug. 1999, pp. 730-741, vol. 52, No. 8.
De Vos, Willem M., et al., "Maturation pathway of nisin and other lantibiotics: post-translationally modified antimicrobial peptides exported by gram-positive bacteria," Molecular Biology, 1995, pp. 427-437, vol. 17, No. 3.
Jack, Ralph, et al., "The genetics of lantibiotic biosynthesis," Bioessays, 1995, pp. 793-802, vol. 17, No. 9.
European Search Report issued in European Patent Application No. EP 10 00 0424 (Apr. 1, 2010).
European Examination issued in European Patent Application No. 07 704 921.1 (Apr. 4, 2010).
International Search Report and Written Opinion in PCT/GB2010/000043 (Mar. 29, 2010).
Widdick et al., "Cloning and engineering of the cinnamycin biosynthetic gene cluster from *Streptomyces cinnamoneus cinnamoneus* DSM 40005", PNAS, 100(7):4316-4321 (Apr. 1, 2003).
Appleyard et al. "NVB302 : Gastrointestinal Stability and in vivo Activity in the Hamster Cecitis Model for *Clostridium difficile* Infection," Poster F1-1520, 49th ICAAC, Sep. 12-15, 2009, San Francisco, USA.
Appleyard et al. "NVB302: A Narrow Spectrum Antibiotic under Development for the Treatment of *Clostridium difficile* Infection," Poster FI-1517, 49th ICAAC, Sep. 12-15, 2009, San Francisco, USA.
Boakes et al., "Organization of the genes encoding the biosynthesis of actagardine and engineering of a variant generation system," Molecular Microbiology, 2009, 72(5), pp. 1126-1136.
European Examination for European Patent Application No. 07704921.1 dated Aug. 30, 2010.
International Search Report and Written Opinion for PCT/GB2010/000042 dated May 20, 2010.
International Search Report and Written Opinion for PCT/GB2010/000188 dated May 20, 2010.
New Zealand Examination Report for New Zealand Patent Application 569486 dated Apr. 27, 2010.
Translation of Israeli Examination Report for Israeli Patent Application No. 192446 dated Apr. 22, 2010.
Wadman et al. "NVB302: In vitro Activity Against *Clostridium difficile* and Intestinal Strains of Anaerobic Bacteria," Poster F1-1518, 49th ICAAC, Sep. 12-15, 2009, San Francisco, USA.
Examination Report in New Zealand Patent Application No. 569486 dated Mar. 10, 2011.
International Preliminary Report on Patentability in PCT/GB2010/000043 dated Apr. 14, 2011.
International Preliminary Report on Patentability in PCT/GB2010/000042 dated Apr. 19, 2011.
International Preliminary Report of the Patentability in PCT/GB2010/000188 dated Apr. 19, 2011.
Boakes et al., "Organization of the biosynthetic genes encoding deoxyactagardine B (DAB), a new lantibiotic produced by *Actinoplanes liguariae* NCIMB41362", The Journal of Antibiotics, 63:351-358 (2010).
Written Opinion of the International Preliminary Examining Authority in PCT/GB2010/000043, dated Feb. 1, 2011.
Wikipedia, the free encyclopedia, "Lanthionine", http://en.wikipedia.org/wiki/Lanthionine, Nov. 2, 2011.
Definition of moiety, from http://dictionary.reference.com/browse/moiety, pp. 1-3. Accessed Aug. 26, 2010.
Rudinger J, "Characterisitics of the amino acids as components of a peptide hormone sequence," Peptide Hormones, JA Parsons Edition, University Park Press, Jun. 1976, pp. 1-7.
"Designing Custom Peptides," from SIGMA Genosys, pp. 1-2, Accessed Dec. 16, 2004.
Schinzel R, Drueckes P, "The phosphate recognition site of *Escherichia coli* maltodextrin phosphorylase," FEBS, Jul. 1991, 286(1,2): 125-128.
Berendsen, "A Glimpse of the Holy Grail?" Science, 1998,282, pp. 642-643.
Bradley et al. "Limits of Cooperativity in a Structually Modular Protein: Response of the Notch Ankyrin Domain to Analogous Alanine Substitutions in Each Repeat," J. Mol. Biol., 2002, 324, pp. 373-386.
Ngo et al. "Computational Complexity, Protein Structure Prediction, and the Levinthal Paradox," The Protein Folding Problem and Tertiary Structure Prediction, K. Merc JT. and S. Le Grand Edition, 1994, pp. 491-495.
Han (Advances in Characterization of Pharmaceutical Hydrates Trends in Bio/Pharmaceutical Industry, pp. 25-29, Mar. 2006).
Vippagunta et al (Adv Drug Deliv Rev 4 8:3-26, 2001).
Voet et al. "Abnormal Hemoglobins," Biochemistry, Second Edition, John Wiley & Sons, Inc., 1995, pp. 235-241.
European Examination of European Patent Application No. 10 000 242.1 dated May 19, 2011.
State Intellectual Property Office of the People's Republic of China, First Office Action for Application No. 20078006748.0, Mar. 23, 2011.
U.S. Office Action on U.S. Appl. No. 12/686,135, dated Apr. 25, 2011.
U.S. Notice of Allowance on U.S. Appl. No. 12/161,221, dated May 12, 2011.
Office Action mailed on Jun. 9, 2013 in corresponding Chinese Application No. 201080016455.2 and an English language translation.
European Examination Report mailed Apr. 12, 2013 in corresponding European Application No. 10702536.3.

\* cited by examiner

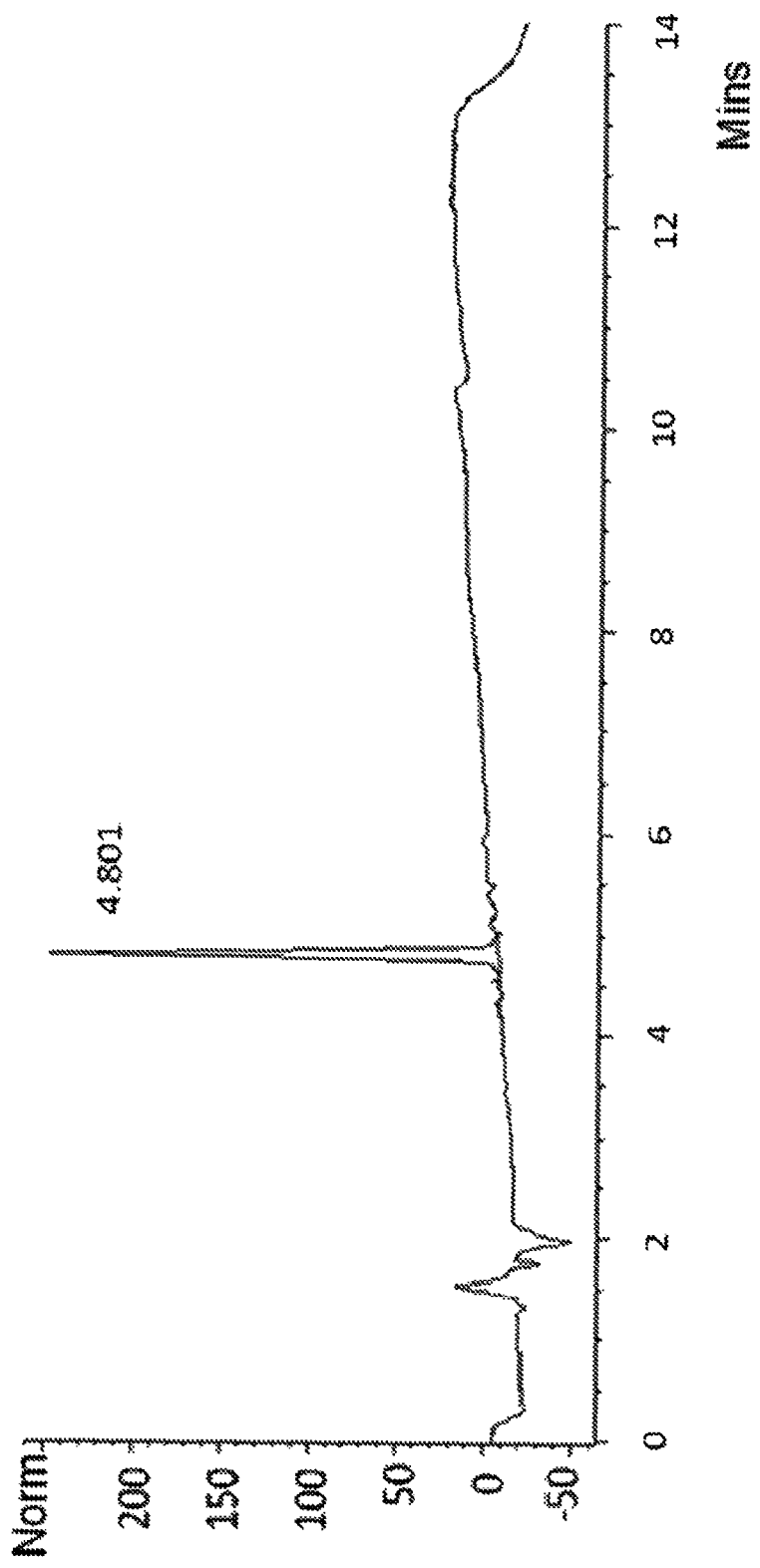

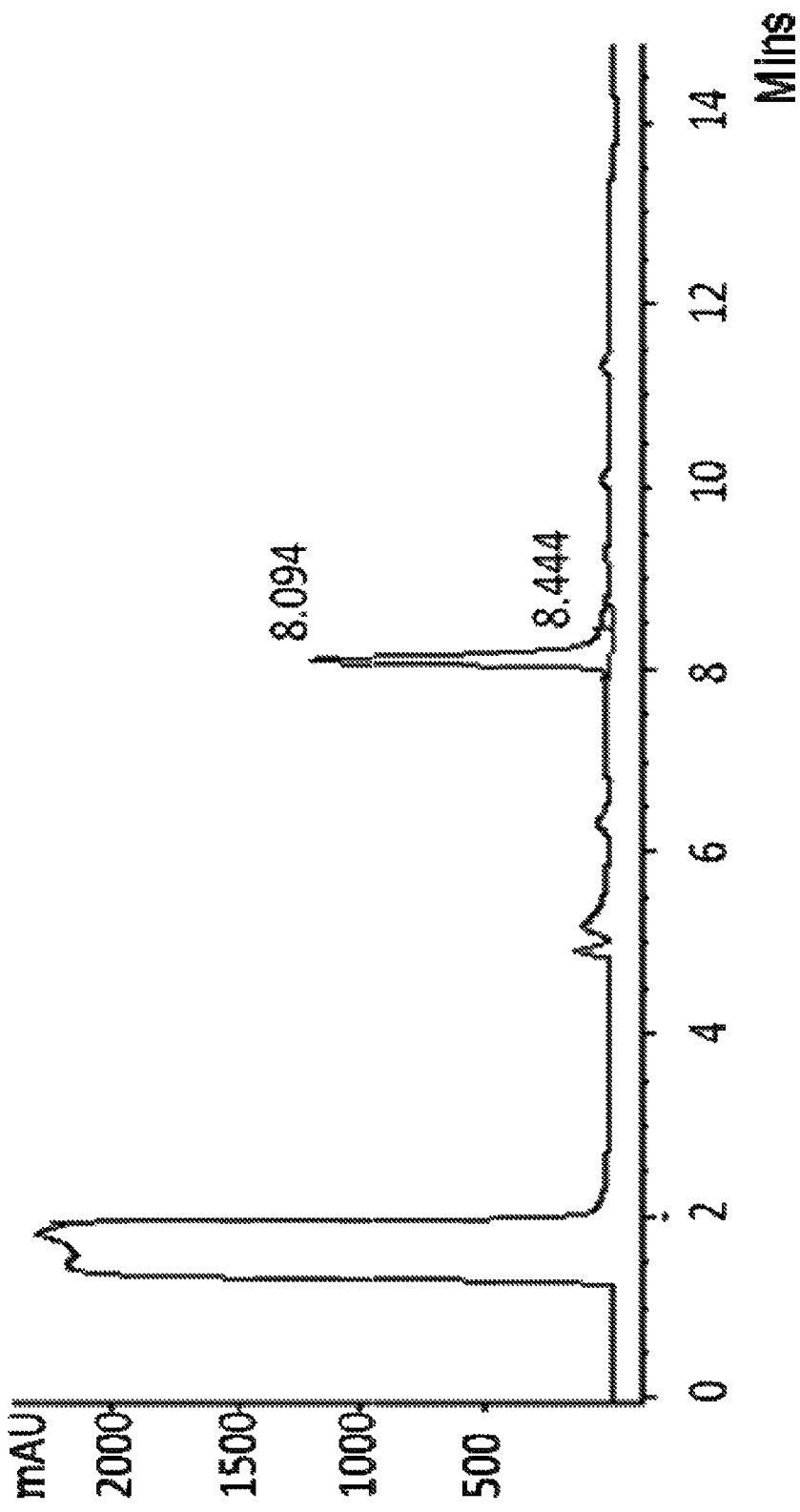
Figure 5 HPLC chromatogram of Example 1 reaction mixture

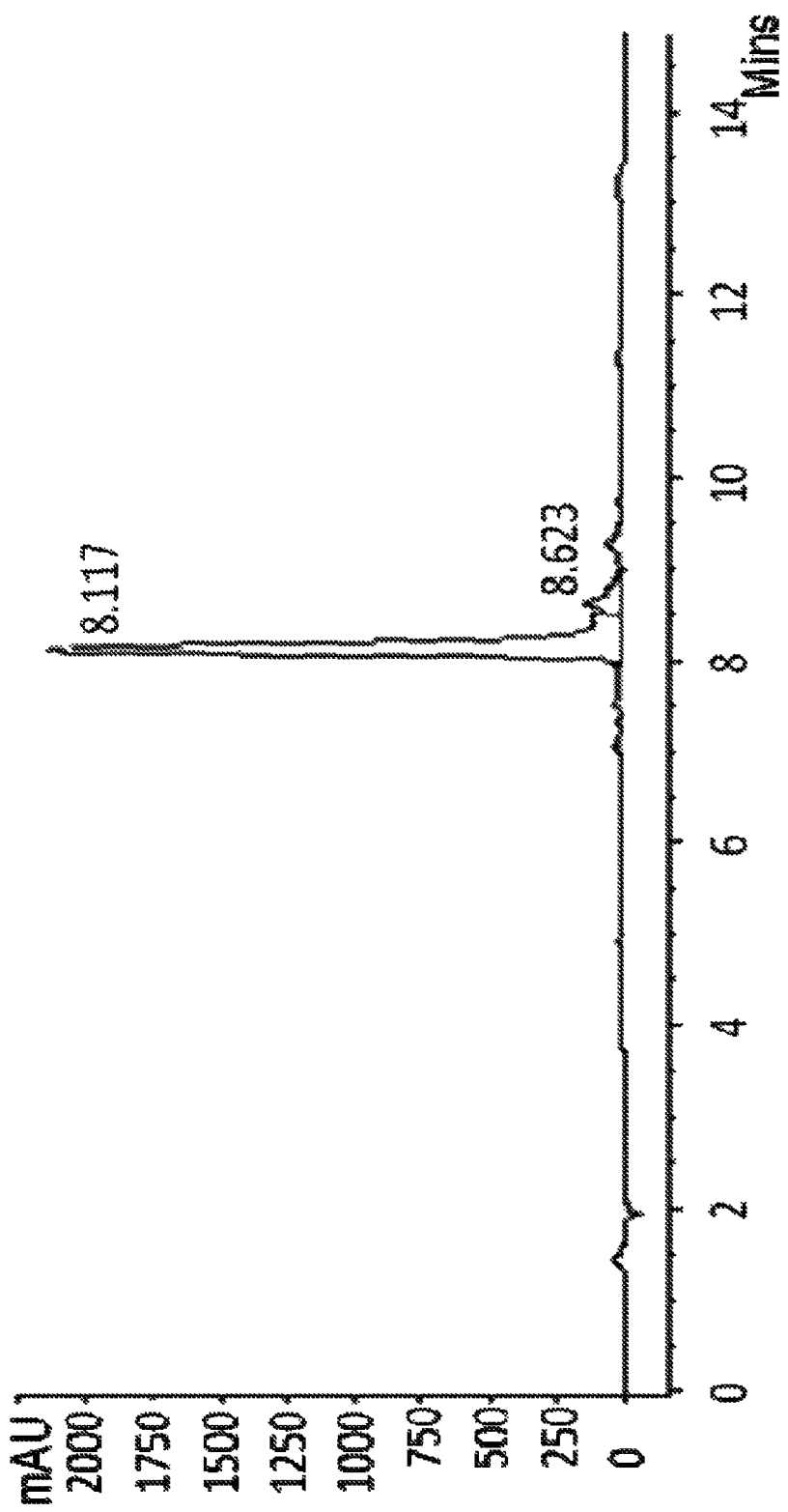

COMPOUNDS

This application is a 371 filing based on PCT/GB2010/000188, filed Feb. 2, 2010, which claims priority to U.S. Provisional Application No. 61/149,857, filed Feb. 4, 2009, all of which are hereby incorporated by reference in their entirety.

The present disclosure relates to certain novel compounds, pharmaceutical compositions comprising same and use of the compounds and compositions for the treatment of microbial infection, particularly Methicillin-resistant *Staphylococcus aureus* (MRSA) infection.

Many antibiotic compounds have been identified from natural sources including microorganisms. Often the antibiotic compounds have a complicated chemical structure and in particular a complicated stereochemical structure.

Actagardine is a natural product prepared from *Actinoplanes garbadinensis*, and has antibiotic properties, see for example EP0195359, in particular against *Streptococcus pyogenes*, which causes scarlet fever and strep throat infection. Despite the need for new antibiotics in the 22 years since publication of EP0195359 no antibiotics derived from actagardine have been licensed and marketed.

A new family of compounds based on deoxyactagardine B was recently disclosed in WO 2007/083112. Deoxyactagardine B is prepared from *A. liguriae* and has a number of distiguishing features from actagardine.

Actagardine activity against MRSA when measured by a standard test, such as minimum inhibitory concentrations (MICs), may be as high as about 32 μg/mL, depending on the strain tested. Thus actagardine has only low to moderate activitity against MRSA because the higher the MIC value the less antimicrobial activity the compound has.

Deoxyactgardine B activity against MRSA when measured by a standard test, such as minimum inhibitory concentrations (MICs), may have an activity as high as about 32 μg/mL, depending on the strain tested. Thus deoxyactagardine has only low to moderate activity against MRSA.

MRSA is a bacterium responsible for difficult-to-treat infections in humans and animals. The particular strain(s) of *Staphylococcus aureus* labeled MRSA is/are resistant to a large group of antibiotics called beta-lactams, which include the penicillins and cephalosporins.

The strain(s) received a significant amount of attention in the media and was branded a "superbug". Patients with open wounds, those who have procedures involving invasive devices, and those with a weakened immune system are most at risk of infection, especially during hospitalization. The infection is highly contagious and if it is identified on a hospital ward, the ward may be closed until it is decontaminated.

Thus antimicrobial compounds with activity against MRSA would be particularly useful.

Certain novel compounds have now been identified with activity against MRSA.

Thus in one aspect there is a provided a compound of formula (I):

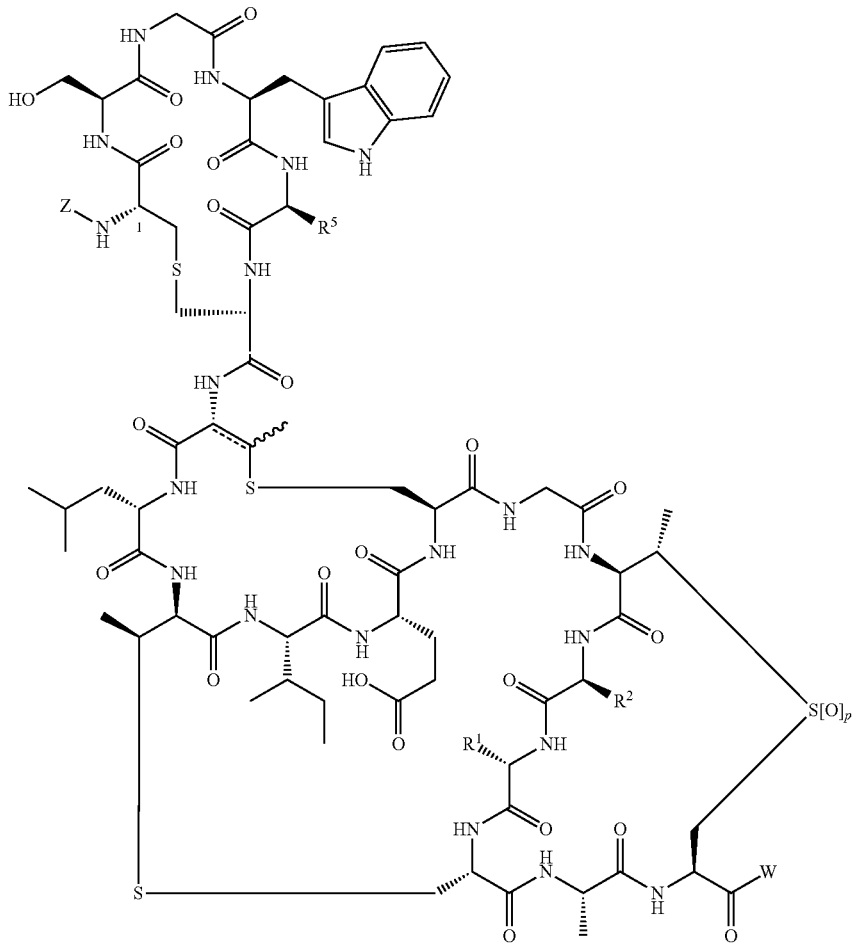

wherein: $R^1$ together with the carbon to which it is attached and the alpha-nitrogen and alpha-carbonyl represents an amino acid residue;

$R^2$ together with the carbon to which it is attached and the alpha-nitrogen and alpha-carbonyl represents an amino acid residue;

W represents —OH or —$XNR^3R^4$;

X represents a bond or an amino acid residue;

$R^3$ represents H or $C_{1-6}$ alkyl;

$R^4$ represents H, $C_{1-6}$ alkyl, —$R^A$-L-$Ar^1$, or $R^3$ together with $R^4$ and the nitrogen to which they are attached form a 5 or 6 membered heterocyclic group optionally including a further heteroatom (for example 1, 2 or 3 further heteroatoms) selected from N, O or S, wherein said heterocyclic group is substituted by Y—$Ar^1$;

$R^A$ represents a bond, —$C_{0-9}$ alkyl$C_{6-10}$aryl, $C_{0-9}$ alkyl$C_{5-11}$ heteroaryl, —$C_{1-9}$ heteroalkyl$C_{5-11}$heteroaryl, —$C_{0-9}$ alkyl$C_{3-6}$cycloalkyl, —$C_{1-9}$ heteroalkyl$C_{5-11}$ heterocyclic or —$C_{0-9}$ alkyl$C_{5-11}$ heterocyclic group;

L represents a straight or branched $C_{0-15}$ alkyl chain wherein optionally one or more carbons (such as 2 or 3) are replaced by a heteroatom independently selected from N, O or S, wherein said chain is optionally substituted by one or more (for example 1 or 2), oxo or nitro groups, with the proviso that a heteroatom is not bonded directly to the N of the group —$NR^3R^4$;

Y represents a straight or branched $C_{0-15}$ alkyl chain wherein optionally one or more carbons (such as 2 or 3) are replaced by a heteroatom independently selected from N, O or S, wherein said chain is optionally substituted by one or more (for example 1 or 2), oxo or nitro groups;

$Ar^1$ represents phenyl substituted by one or two $NO_2$ groups or one to five (such as 2, 3, or 4) halogen groups or one or two $C_{1-3}$ haloalkyl groups, or a combination thereof;

$R^5$ together with the carbon to which it is attached and the alpha-nitrogen and alpha-carbonyl represents an amino acid residue:

Z represents H, $C_{1-6}$ alkyl, an amino acid residue or —$R^B$-Q-$Ar^2$;

$R^B$ represents a bond, —$C_{0-9}$ alkyl$C_{6-10}$aryl, —$C_{0-9}$ alkyl $C_{6-11}$heteroaryl, —$C_{0-9}$ alkyl$C_{3-6}$cycloalkyl, —$C_{0-9}$ alkyl$C_{5-11}$ heterocycle;

Q represent a straight or branched $C_{0-15}$ alkyl chain wherein optionally one or more carbons (such as 2 or 3) are replaced by a heteroatom independently selected from N, O or S, wherein said chain is optionally substituted by one or more (for example 1 or 2) oxo or nitro groups;

$Ar^2$ represents phenyl substituted by one or two $NO_2$ groups or one to five (such as 2, 3, or 4) halogen groups or a combination thereof;

p represents 0 or 1; and the fragment:

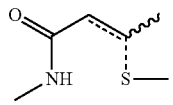

represents:

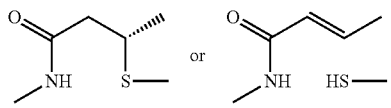

or the E isomer of the latter, wherein said compound of formula (I) comprises at least an $Ar^1$ group or an $Ar^2$ group.

The compounds of the present disclosure have activity against MRSA (Methicillin resistant *Staphylococcus aureus*), for example R33, 12232, R36, R34, R39, R37, R31, R40, W71, W74, W82, W96, W97, W98 and/or W99, when measured by a standard test e.g. MIC.

Furthermore the compounds have activity against Methicillin sensitive *Staphylococcus aureus*, for example G15, G20, G22, G23, G28, G30, G31, G32, G33, G35, G12, G26, G29, SH1000 and/or 8325-4, when measured by a standard test, such as MIC.

In one embodiment the compounds of the present disclosure advantageously have an activity against one or more strains of MRSA of 8 μg/mL or less, such as 4 or 2 μg/mL, which represents at least a 2 fold, such as a 3 or 4 fold, increase in activity over the parent actagardine or deoxyactagardine B compounds.

This is particularly surprising because compounds derived from a "parent" compound have worse activity than the parent compound, for example deoxyactagardine B N-[1-(1-methyl-4-piperidinyl)piperazine]monocarboxamide and deoxyactagardine B N-[1-(3-dimethylamino propyl)piperazine]monocarboxamide have an MIC against *Stapholococcus aureus* strains R33 and SH1000 of approximately 64 μL/mL, that is to say they have poor activity against MRSA. Whilst not wishing to be bound by theory it is thought that the specifically substituted phenyl moiety characterising the compound of the present disclosure contributes significantly the special properties observed herein.

The compounds of the present disclosure have activity against a number of microbes, for example those listed herein, which may make them suitable for use as broad spectrum antibiotics, for example the compounds of the present disclosure generally have antimicrobial activity against Vancomycin intermediate *Staphylococcus aureus* for example strains V99, MI, Mu3, 26, Mu50, 2, NJ, and/or vancomycin sensitive or resistant enterococci, for example *E. faecalis* 7754422, GRL05022, GRL05023, GRL05024, GRL05026, GRL05027, GRL05029, GRL05030, GRL05031, GRL05032, GRL05033, GRL05034, GRL05035, 7757400, 9758512 and/or 7791220 or *E. faecium* 7865229, 19579, 7662769, 7634337, 7865532, 9709024, 9710577, 9704998, and/or 7860190, when measured by a standard test, such as MIC.

Thus compounds of the disclosure have activity against *Staphylococcus aureus* and may additionally or alternatively have activity against enterococci, and/or *S. pyogenes* and/or *Streptococcus pneumoniae*.

BRIEF DESCRIPTION OF THE DRAWINGS

FIG. 4 is a HPLC chromatogram of Deoxyactagardine B.

FIG. 5 is a HPLC chromatogram of Example 1 reaction mixture.

FIG. 6 is a HPLC chromatogram of Example 1 after purification.

DETAILED DESCRIPTION

Figure 1:
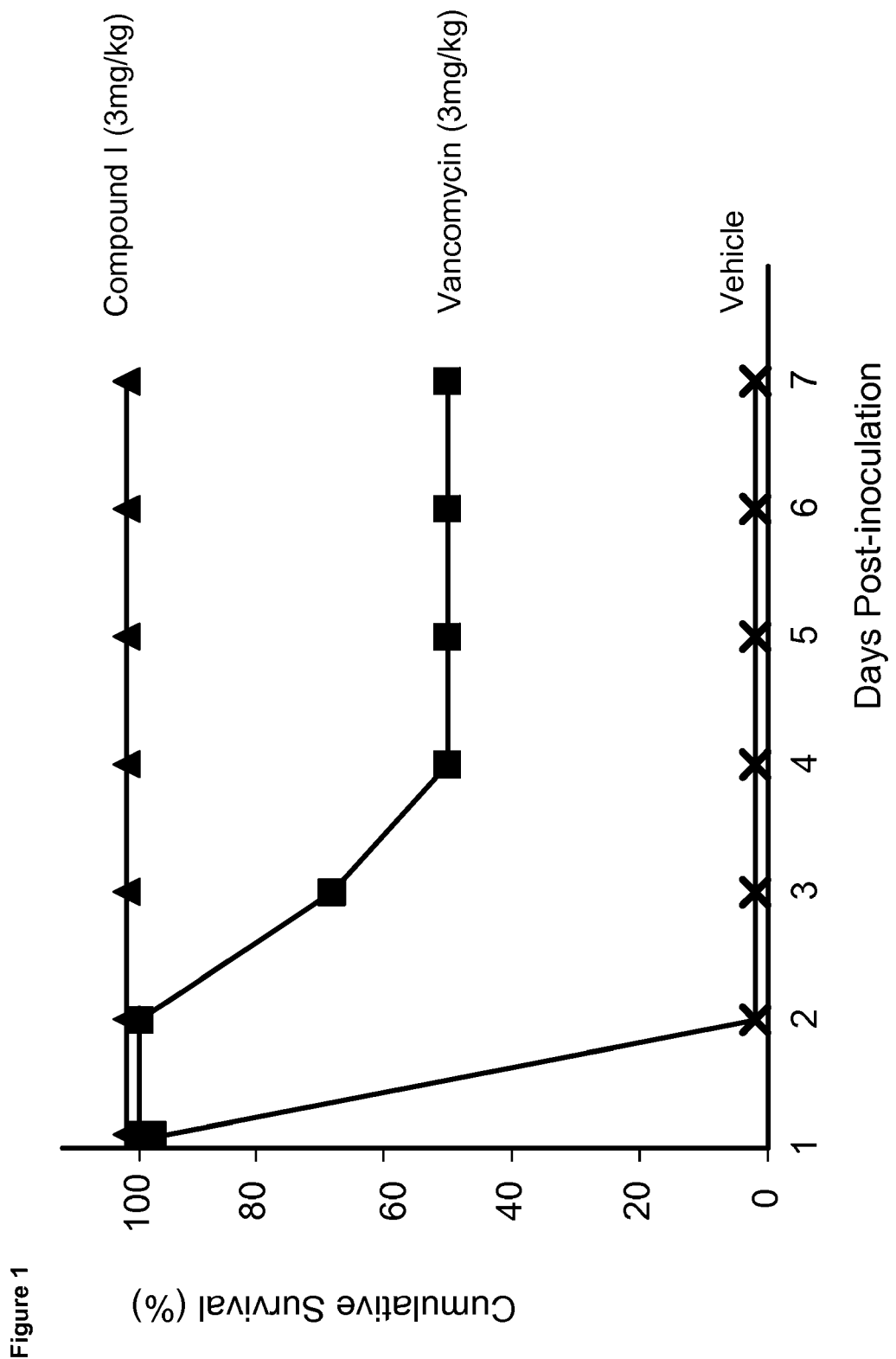
FIG. 1 shows the activity of the compound of Example 1a in a mouse bacteraemia model for *Staphylococcus aureus* methicillin resistant (ATCC 33591) as a function of cumulative survival rate over time (post-inoculation). (▲) represents the compound of Example 1, (■) represents vancomycin, and (✹) represents the vehicle. The compound of Example 1a and vancomycin were administered subcutaneously (both 3 mg/Kg).

Alkyl in the context of the present disclosure refers to straight chain or branched chain alkyl, for example methyl, ethyl, n-propyl, isopropyl, n-butyl or t-butyl.

Heterocyclic group as employed herein is a saturated or partially unsaturated ring (i.e. a non-aromatic mono or bicyclic ring) comprising one or more heteroatoms selected from O, N and S, for example a 5 or 6 membered heterocycle group such as pyrroline (in particular 1, 2 or 3-pyrroline), pyrrolidine, tetrahydrofuran, tetrahydrothiophene, pyrazoline (in particular 2 or 3-pyrazoline), 2-imidazoline, pyrazolidine, imidazolidine, 3-dioxolane, thiazolidine, isoxazolidine, pyran (in particular 2H or 4H-pyran), 3,4-dihydro-2H-pyran, piperidine, 1,4-oxazine, 1,4-dioxine, piperazine, morpholine, 1,4-dioxane. It will be understood that in definitions employed herein, such as $C_{5-11}$ heterocycle, that the heteroatom may replace a carbon atom in the ring and therefore $C_{5-11}$ heterocycle and a 5 to 11 membered heterocycle are used interchangeably. Other definitions of heterocycles will be construed similarly. The heterocycle may be linked through carbon or nitrogen.

Cycloalkyl as employed herein refers to a saturated or partially unsaturated carbocyclic ring, i.e. a non-aromatic carbocyclic ring, for example cyclopropyl, cyclopentyl or cyclohexyl.

Heteroaryl as employed herein refers to an aromatic carbocycle comprising one or more heteroatoms selected from O, N or S including a bicyclic system wherein one or both rings are aromatic, for example a 5-11 membered heteroaryl, such as pyrrole, furan, thiophene, pyrazole, imidazole, oxazole, isoxazole, thiazole, isothiazole, triazole, oxadiazole, furazan, tetrazole, pyridine, pyridazine, pyrimidine, pyrazine, triazine, 1H-pyrrolizine, indolizine, indole, isoindole, benzofuran, isobenzofuran, indoline, isoindoline, benzothiophene, indazole, benzimidazole, purine, quinoline, isoquinoline, chromane, isochromane, chromene, cinnoline, quinazoline, quinoxaline, naphthyridine or phthalazine. It will be understood that in definitions employed herein, such as $C_{5-11}$ heteraryl, that the heteroatom may replace a carbon atom in the ring and therefore $C_{5-11}$ heteroaryl and a 5 to 11 membered heteroaryl are used interchangeably. Other definitions of heteroaryls will be construed similarly. The heteroaryl may be linked through carbon or a nitrogen, as appropriate, in particular carbon.

Halogen as employed herein refers to fluoro, chloro or bromo, such as fluoro or chloro.

Haloalkyl as employed herein refers to alkyl groups having 1 to 6 halogen atoms, for example 1 to 5 halogens, such as per haloalkyl, in particular perfluoroalkyl, more specifically —$CCl_2CCl_3$, $CCl_3$, —$CF_2CF_3$ or —$CF_3$.

Heteroalkyl as employed herein is an alkyl represents a straight or branched $C_{0-15}$ alkyl chain wherein optionally one or more carbons (such as 2 or 3) are replaced by a heteroatom independently selected from N, O or S, wherein said chain is optionally substituted by one or more (for example 1 or 2), oxo or nitro groups.

In relation to a saturated or unsaturated, branched or unbranched alkyl chain, wherein a carbon is replaced by a heteroatom selected from O, N or S, it will be clear to persons skilled in the art that the heteroatom may replace a primary, secondary or tertiary carbon, that is —$CH_3$, —$CH_2$—, a —CH— or a branched carbon group, as technically appropriate.

In one embodiment $Ar^1$ represents phenyl substituted by one or two $NO_2$ groups or one to five (such as 2, 3, or 4) halogen groups, or a combination thereof.

In one embodiment $R^1$ together with the carbon to which it is attached and the alpha-nitrogen and alpha-carbonyl is a natural amino acid.

In one embodiment $R^1$ together with the carbon to which it is attached and the alpha-nitrogen and alpha-carbonyl is an amino acid residue selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine, for example phenylalanine, valine, leucine or isoleucine, such as valine, leucine or isoleucine, in particular valine.

In one embodiment $R^2$ together with the carbon to which it is attached and the alpha-nitrogen and alpha-carbonyl is a natural amino acid.

In one embodiment $R^2$ together with the carbon to which it is attached and the alpha-nitrogen and alpha-carbonyl is an amino acid residue selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine, for example phenylalanine, valine, leucine or isoleucine, such as valine, leucine or isoleucine, in particular leucine.

In one embodiment $R^1$ is valine and $R^2$ is leucine.

In one embodiment $R^1$ is isoleucine and $R^2$ is valine.

In one embodiment X represents a bond. When X is a bond then it is to be understood that the nitrogen of —$NR^3R^4$ will be attached directly to the carbon of the carbonyl.

In an alternative embodiment X is a natural amino acid, for example selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine, such as arginine.

In one embodiment $R^3$ represents H. In an alternative embodiment $R^3$ represent methyl, ethyl, propyl or butyl.

In one embodiment $R^4$ is H. In an alternative embodiment $R^4$ represent methyl, ethyl, propyl or butyl. In one embodiment, when $R^4$ represents H or $C_{1-6}$ alkyl, then Z represents —$R^B$-Q-$Ar^2$. In an alternative embodiment $R^4$ represents —$R^A$-L-$Ar^1$.

When $R^4$ represents —$R^A$-L-$Ar^1$, Z may for example represent H, $C_{1-6}$ alkyl or an amino acid residue. In an alternative embodiment $R^4$ is —$R^A$-L-$Ar^1$ and Z represents —$R^B$-Q-$Ar^2$.

In another alternative embodiment $R^3$ and $R^4$ together with the nitrogen to which they are attached form a 5 or 6 membered heterocyclic group optionally including a further heteroatom (for example 1, 2, or 3) selected from N, O, and S, for example pyrrolidine, piperidine, piperazine, such as piperazine or piperidine.

In one embodiment $R^A$ represents a bond, —$C_{0-9}$ alkyl $C_{6-10}$aryl, —$C_{0-9}$ alkyl$C_{5-11}$heteroaryl, —$C_{0-9}$ alkyl$C_{3-6}$cloalkyl or a —$C_{0-9}$ alkyl$C_{5-11}$ heterocyclic group.

In one embodiment $R^4$ is a bond. When $R^4$ is a bond then it will be understood that L or $Ar^1$, as appropriate, is directly linked to the nitrogen of —$NR^3R^4$.

In one embodiment $R^4$ is $C_{0-9}$ alkyl$C_{6-10}$aryl, such as $C_1$ alkyl-, $C_2$ alkyl-, $C_3$ alkyl-, $C_4$ alkyl-, $C_5$ alkyl-, $C_6$ alkyl-, $C_7$ alkyl- or $C_8$ alkyl-phenyl or napthyl, in particular phenyl. When $C_0$ is employed then $C_{6-10}$aryl will be linked directly to the nitrogen of —$NR^3R^4$.

In an alternative embodiment $R^4$ is $C_{0-9}$ alkyl$C_{5-11}$heteroaryl, $C_{0-9}$ alkyl$C_{3-6}$cycloalkyl, or a —$C_{0-9}$ alkyl$C_{5-11}$ heterocyclic group.

In an alternative embodiment $R^4$ is $C_{0-3}$ alkyl$C_{5-11}$heteroaryl, such as $C_1$ alkyl-, $C_2$ alkyl-, $C_3$ alkyl-, $C_4$ alkyl-, $C_5$ alkyl-, $C_6$ alkyl-, $C_7$ alkyl- or $C_8$ alkyl-heteroaryl, for example selected from pyrrole, furan, thiophene, pyrazole, imidazole, oxazole, isoxazole, thiazole, isothiazole, triazole, oxadiazole, furazan, tetrazole, pyridine, pyridazine, pyrimidine, pyrazine, triazine, 1H-pyrrolizine, indolizine, indole, isoindole, benzofuran, isobenzofuran, indoline, isoindoline, benzothiophene, indazole, benzimidazole, purine, quinoline, isoquinoline, chromane, isochromane, chromene, cinnoline, quinazoline, quinoxaline, naphthyridine or phthalazine.

In one embodiment $R^4$ is $C_{0-9}$ alkyl$C_{3-6}$cycloalkyl, for example $C_1$ alkyl-, $C_2$ alkyl-, $C_3$ alkyl-, $C_4$ alkyl-, $C_5$ alkyl-, $C_6$ alkyl-, $C_7$ alkyl- or $C_8$ alkyl-$C_{3-6}$cycloalkyl selected for cyclopropyl, cyclopentyl or cyclohexyl. When $C_0$ is employed then $C_{3-6}$cycloalkyl will be linked directly to the nitrogen of —$NR^3R^4$.

In one embodiment $R^4$ is —$C_{0-9}$ alkyl$C_{5-11}$ heterocyclic group for example $C_1$ alkyl-, $C_2$ alkyl-, $C_3$ alkyl-, $C_4$ alkyl-, $C_5$ alkyl-, $C_6$ alkyl-, $C_7$ alkyl- or $C_8$ alkyl-heterocyclic group for example selected from pyrroline (such as 1, 2 or 3-pyrroline), pyrrolidine, tetrahydrofuran, tetrahydrothiophene, pyrazoline (such as 2 or 3-pyrazoline), 2-imidazoline, pyrazolidine, imidazolidine, 3-dioxolane, thiazolidine, isoxazolidine, pyran (such as 2H or 4H-pyran), 3,4-dihydro-2H-pyran, piperidine, 1,4-oxazine, 1,4-dioxine, piperazine, morpholine and 1,4-dioxane. When $C_0$ is employed then $C_{5-11}$ heterocycle will be linked directly to the nitrogen of —$NR^3R^4$.

Clearly $R^4$ is a linking group and thus when it comprises a ring such as a cycloalkyl, heterocycle, heteroaryl or aryl then $LAr^1$ may be attached via the ring.

L in one embodiment is $C_0$. When L is $C_0$ the $Ar^1$ may be linked directly to the nitrogen of —$NR^3R^4$. Alternatively when L is $C_0$ then $Ar^1$ may be linked to $R^4$.

In an alternative embodiment L is a straight or branched, such as straight, $C_{1-9}$ alkyl chain wherein optionally one or more, such as one, carbon(s) is/are replaced by a heteroatom selected from O, N and S, such as N, and optionally substituted by oxo (e.g. 1 or 2). For example L is a straight $C_{1-3}$ alkyl chain (such as $C_1$ alkyl), wherein none of the carbons are replaced by a heteroatom, e.g. wherein the chain does not bear any optional substituents.

Alternatively, L is a straight $C_{6-9}$ alkyl chain, wherein one carbon is replaced by a heteroatom, such as N, and the chain optionally bears one oxo substituent, in particular —$(CH_2)_i$ $NH(CH_2)_j$ or —$(CH_2)_k$NHC(O)— wherein i is an integer 1 to 12, j is 0 or 1 and k is and integer 1 to 14 such as —$CH_2CH_2CH_2NHCH_2$— or —$CH_2CH_2CH_2NHC(O)$—.

In one embodiment a heteroatom in L is separate from the nitrogen of —$NR^3R^4$ by at least two carbon atoms.

In one embodiment Y represents $C_0$. When Y is $C_0$ the $Ar^1$ will be linked directly to the relevant heterocycle group.

In an alternative embodiment Y is a straight or branched, such as straight, $C_{1-5}$ alkyl chain (for example $C_2$, $C_3$ or $C_4$ chain, such as a $C_4$ alkyl chain) wherein optionally one or more, such as one, carbon(s) is/are replaced by a heteroatom selected from O, N and S, such as N, and optionally substituted by oxo (for example 1 or 2 oxo substituents, in particular on carbon), such as —$CH_2$— or —$CH_2CH_2NHC(O)$—.

In one embodiment $Ar^1$ is phenyl substituted by 1, 2, 3, 4, or 5 halogen groups, for example: 1 halogen group, such as 2-chloro, 3-chloro, 4-chloro, 2-fluoro, 3-fluoro, 4-fluoro; 2 halogen groups, such as di-fluoro, di-chloro, di-bromo (such as 2,3; 2,4; 2,5; 2,6; 3,4; 3,5 halo); or 3 halogen groups such as tri-fluoro or tri-chloro; in particular 4-chloro, 3,5 di-chloro, 3,4 di-chloro, 2,4 di-chloro, 3,5 di-fluoro, 3,4 di-fluoro, 2,4-di-fluoro, 2-fluoro4-bromo, especially 4-chloro, 3,5 di-chloro, 3,4 di-chloro, 2,4-di-chloro or 2,4-di-fluoro.

In an alternative embodiment $Ar^1$ is phenyl substituted by one or two nitro groups such as 2,3; 2,4; 2,5; 2,6; 3,4; 3,5 di-nitro, e.g. 2-nitro, 3-nitro, 4-nitro, 3,5-nitro, 3,4-nitro or 2,4-nitro.

In one embodiment $Ar^1$ is phenyl substituted by 1, 2, 3 or 4 halogens and 1 or 2 nitro groups, with the proviso that the phenyl bears at most 5 substituents.

In an alternative embodiment $Ar^1$ is phenyl substituted by one or two haloalkyl groups, for example 2-haloalkyl, 3-haloalkyl, 4-haloalkyl, 3,5 di-haloalkyl, 3,4 di-haloalkyl, 2,4-di-haloalkyl, especially wherein the haloalkyl is —$CF_3$.

In one embodiment the fragment —$NR^3R^4$ represents -piperazinyl($CH_2$)$_n$phenyl wherein phenyl is substituted by one or two $NO_2$ groups or one to five (such as 2, 3, or 4) halogen groups, for example as defined above, and n represents 0 or 1.

In one embodiment the fragment —$NR^3R^4$ represents -piperazinyl($CH_2$)$_n$phenyl wherein phenyl is substituted by one or two haloalkyl groups, for example as defined above, and n represents 0 or 1.

In one embodiment the fragment —$NR^3R^4$ is -piperazinyl substituted in the 4 position by —$CH_2$phenyl the latter bearing one or two groups selected from $NO_2$, chloro and bromo. In one embodiment the fragment —$NR^3R^4$ does not represent -piperazinyl substituted in the 4 position by —$CH_2$phenyl wherein phenyl is substituted by one or two groups selected from $NO_2$, chloro and bromo, in particular wherein the scaffold is actagardine.

In one embodiment the compound is not actagardine [4-(4'-bromobenzyl)piperazine]monocarboxamide, actagardine [4-(4'-chlorobenzyl)piperazine]monocarboxamide or actagardine [4-(4'-nitrobenzyl)piperazine]monocarboxamide In one aspect the fragment —$NR^3R^4$ represents -piperazinyl$CH_2CH_2NHC(O)$phenyl, wherein phenyl is substituted by one or two $NO_2$ groups or one to five (such as 2, 3, or 4) halogen groups, for example as defined above.

In one aspect the fragment —$NR^3R^4$ represents -piperazinyl$CH_2CH_2NHC(O)$phenyl, wherein phenyl is substituted by one or two haloalkyl groups, for example as defined above.

In one embodiment $R^5$ represents a natural amino acid residue, for example selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine, such as phenylalanine, valine, leucine or isoleucine, in particular valine or leucine.

In one embodiment Z represents H, $C_{1-6}$ alkyl, for example methyl, ethyl, propyl or butyl, or an amino acid residue, for example selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine, such as alanine or serine.

In one embodiment Z is H or ala, such as H. In one embodiment Z is phenylalanine.

In an alternative embodiment Z represents —$R^B$-Q-Ar$^2$.

In one embodiment $R^B$ is a bond. When $R^B$ is a bond then it will be understood that Q or Ar$^2$, as appropriate, is directly linked to the terminal nitrogen of the amino acid at position 1.

In an alternative embodiment $R^B$ is $C_{0-9}$ alkyl$C_{6-10}$aryl, such as $C_1$ alkyl-, $C_2$ alkyl-, $C_3$ alkyl-, $C_4$ alkyl-, $C_5$ alkyl-, $C_6$ alkyl-, $C_7$ alkyl- or $C_8$ alkyl-phenyl or napthyl, in particular phenyl. When $C_0$ is employed then $C_{6-10}$aryl will be linked directly to the terminal nitrogen of the amino acid at position 1.

In an alternative embodiment $R^B$ is —$C_{0-9}$ alkyl $C_{6-10}$heteroaryl, such as $C_1$ alkyl-, $C_2$ alkyl-, $C_3$ alkyl-, $C_4$ alkyl-, $C_5$ alkyl-, $C_6$ alkyl-, $C_7$ alkyl- or $C_8$ alkyl-heteroaryl, wherein said heteroaryl is selected, for example from pyrrole, furan, thiophene, pyrazole, imidazole, oxazole, isoxazole, thiazole, isothiazole, triazole, oxadiazole, furazan, tetrazole, pyridine, pyridazine, pyrimidine, pyrazine, triazine, 1H-pyrrolizine, indolizine, indole, isoindole, benzofuran, isobenzofuran, indoline, isoindoline, benzothiophene, indazole, benzimidazole, purine, quinoline, isoquinoline, chromane, isochromane, chromene, cinnoline, quinazoline, quinoxaline, naphthyridine or phthalazine. When $C_0$ is employed then $C_{5-10}$heteroaryl will be linked directly to the terminal nitrogen of the amino acid at position 1.

In one embodiment $R^B$ is —$C_{0-9}$ alkyl$C_{3-6}$cycloalkyl, for example $C_1$ alkyl-, $C_2$ alkyl-, $C_3$ alkyl-, $C_4$ alkyl-, $C_5$ alkyl-, $C_6$ alkyl-, $C_7$ alkyl- or $C_8$ alkyl-$C_{3-6}$cycloalkyl, wherein said cycloalkyl is selected from cyclopropyl, cyclopentyl or cyclohexyl. When $C_0$ is employed then $C_{3-6}$cycloalkyl will be linked directly to the terminal nitrogen of the amino acid at position 1.

In one embodiment $R^B$ is $C_{0-9}$ alkyl$C_{6-11}$ heterocyclic group for example $C_1$ alkyl-, $C_2$ alkyl-, $C_3$ alkyl-, $C_4$ alkyl-, $C_5$ alkyl-, $C_6$ alkyl-, $C_7$ alkyl- or $C_8$ alkyl-heterocyclic group, for example wherein said heterocyclic group is selected from pyrroline (such as 1, 2 or 3-pyrroline), pyrrolidine, tetrahydrofuran, tetrahydrothiophene, pyrazoline (such as 2 or 3-pyrazoline), 2-imidazoline, pyrazolidine, imidazolidine, 3-dioxolane, thiazolidine, isoxazolidine, pyran (such as 2H or 4H-pyran), 3,4-dihydro-2H-pyran, piperidine, 1,4-oxazine, 1,4-dioxine, piperazine, morpholine and 1,4-dioxane. When $C_0$ is employed then $C_{5-11}$ heterocycle will be linked directly to the terminal nitrogen of the amino acid at position 1.

Q in one embodiment is $C_0$. When Q is $C_0$ then it will be understood that Ar$^2$ may be directly linked to the terminal nitrogen of the amino acid at position 1.

In an alternative embodiment Q is a straight or branched, such as straight, $C_{1-9}$ alkyl chain wherein optionally one or more, such as one, carbon(s) is/are replaced by a heteroatom selected from O, N and S, such as N, and optionally substituted by oxo. For example Q is a straight $C_{1-3}$ alkyl chain (such as $C_1$ alkyl), wherein none of the carbons are replaced by a heteroatom, in particular wherein the chain does not bear any optional substituents.

Alternatively, Q is a straight $C_{6-9}$ alkyl chain, wherein one carbon is replaced by a heteroatom, such as N, and the chain optionally bears one oxo substituent, in particular —(CH$_2$)$_f$-NH(CH$_2$)$_g$ or —(CH$_2$)$_h$NHC(O)— wherein f is an integer 1 to 12, g is 0 or 1 and h is and integer 1 to 14, such as —CH$_2$CH$_2$CH$_2$NHCH$_2$— or —CH$_2$CH$_2$CH$_2$NHC(O)—.

In one embodiment Ar$^2$ is phenyl substituted by 1, 2, 3, 4 or 5, such as 2 halogen groups, for example di-fluoro, di-chloro or di-bromo, in particular 4-chloro, 3,5-di-chloro, 3,4 di-chloro, 2,4-di-chloro or 2,4-di-fluoro. In an alternative embodiment Ar$^2$ is phenyl substituted by one or two nitro groups, for example 4-nitro, 3,5-nitro, 3,4-nitro or 2,4-nitro.

In one embodiment p is 0. In one embodiment p is 1.

In one embodiment the fragment:

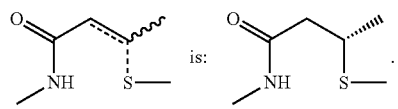

In an alternative embodiment the fragment:

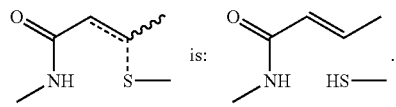

In one embodiment W represents —OH.

In one embodiment there is provided a compound of formula (II) comprises at least an Ar$^1$ group or an Ar$^2$ group wherein $R^1$, $R^2$, $R^3$, $R^4$, $R^5$, Z and p are defined above:

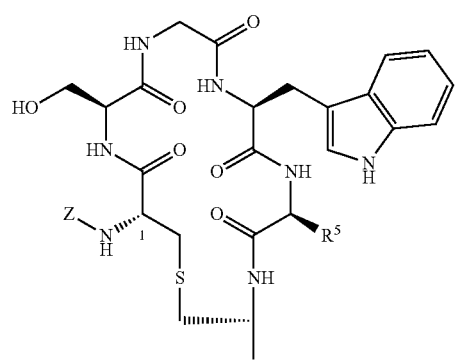

(II)

-continued
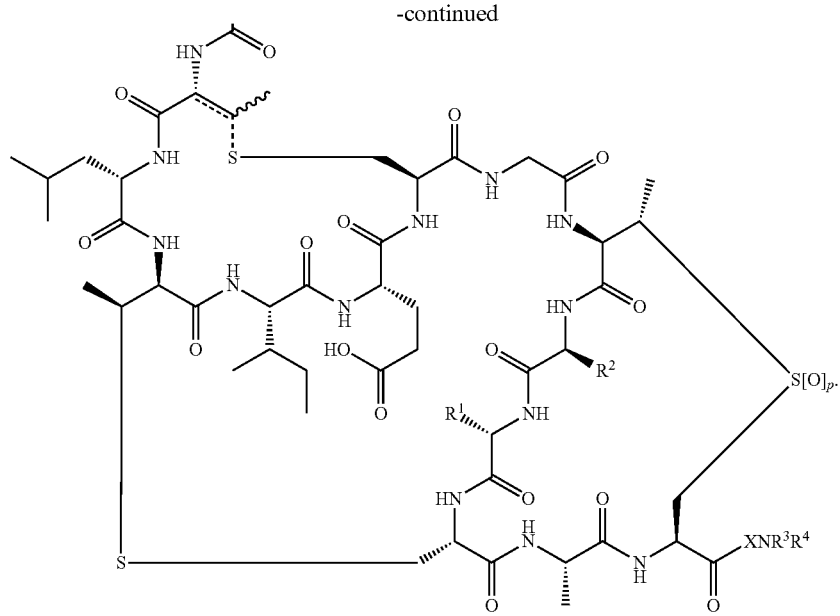
In one embodiment there is provided a compound which has a formula (III) wherein $R^1$, $R^2$, Z, $YAr^1$ and p are as defined above for compounds of formula (I) and said compound of formula (III) comprises at least an $Ar^1$ group or an $Ar^2$ group:
(III)
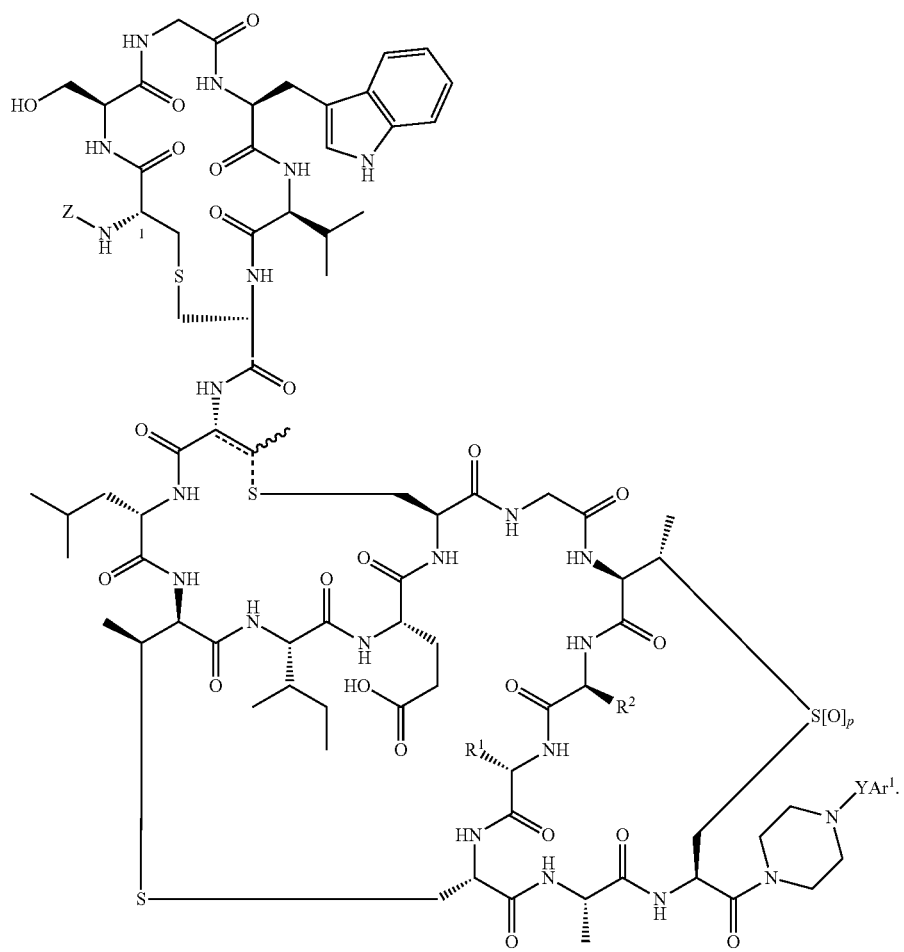

In one embodiment there is provided a compound of formula (IV):

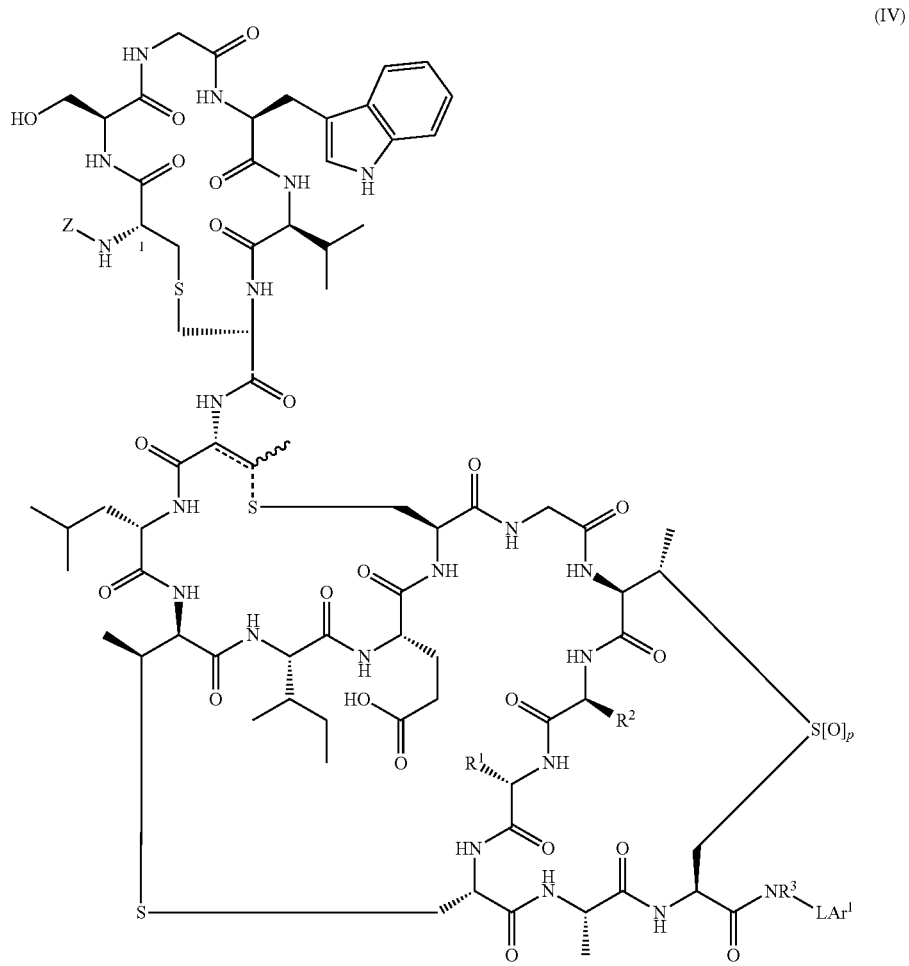

(IV)

wherein R¹, R², R³, Z, L and Ar¹ are defined above for compounds of formula (I) and said compound of formula (IV) comprises at least an Ar¹ group or an Ar² group.

Various aspects of the disclosure are provided in paragraphs 1 to 64 below.

Paragraph 1 in one aspect there is provided a compound of formula (I), as defined above wherein:

$R^1$ together with the carbon to which it is attached and the alpha-nitrogen and alpha-carbonyl represents an amino acid residue, $R^2$ together with the carbon to which it is attached and the alpha-nitrogen and alpha-carbonyl represents an amino acid residue, W represents —OH or —XNR³R⁴, X represents a bond or an amino acid residue, $R^3$ represents H or $C_{1-6}$ alkyl, $R^4$ represents H, $C_{1-6}$ alkyl, —R⁴-L-Ar¹, or $R^3$ together with $R^4$ and the nitrogen to which they are attached form a 5 or 6 membered heterocyclic group optionally including a further hetero atom selected from N, O or S, substituted by YAr¹, $R^A$ represents a bond, $C_{0-9}$ alkyl$C_{6-10}$aryl, —$C_{0-9}$ alkyl $C_{6-11}$heteroaryl, —$C_{0-9}$ alkyl$C_{3-6}$cycloalkyl, —$C_{0-9}$ alkyl$C_{6-11}$ heterocycle group;

L represents a straight or branched $C_{0-15}$ alkyl chain wherein optionally one or more carbons (such as two or three) are replaced by a heteroatom independently selected from N, O or S, wherein a carbon in said chain is optionally substituted by one or more, oxo or nitro groups with the proviso that a heteroatom is not bonded directly to the N of the group —NR³R⁴;

Y represents a straight or branched $C_{0-15}$ alkyl chain wherein optionally one or more carbons (such as two or three) are replaced by a heteroatom independently selected from N, O or S, wherein a carbon in said chain is optionally substituted by one or more oxo or nitro groups;

Ar¹ represents phenyl substituted by one or two NO₂ groups or one to five such as 2, 3, or 4 halogen groups;

$R^5$ together with the carbon to which it is attached and the alpha-nitrogen and alpha-carbonyl represents an amino acid, Z represents H, $C_{1-6}$ alkyl, an amino acid residue or —$R^B$-Q-Ar²;

$R^B$ represents a bond, —$C_{0-9}$ alkyl$C_{6-10}$aryl, —$C_{0-9}$ alkyl $C_{6-10}$heteroaryl, —$C_{0-9}$ alkyl$C_{3-6}$cycloalkyl, —$C_{0-9}$ alkyl $C_{5-10}$ heterocyclyl;

Q represent a straight or branched $C_{0-15}$ alkyl chain wherein optionally one or more carbons (such as two or three) are replaced by a heteroatom independently selected from N, O or S, wherein a carbon in said chain is optionally substituted by one or more halogen, oxo or nitro groups Ar² represents phenyl substituted by one or two NO₂ groups or one to five such as 2, 3, or 4 halogen groups;

p represents 0 or 1; and the fragment:

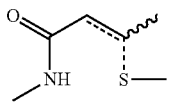

represents:

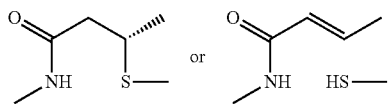

or the E isomer of the latter, with the proviso that a compound of formula (I) comprise at least an Ar¹ group or an Ar² group.

Paragraph 2 in one aspect there is provided a compound of formula (I) according to paragraph 1, wherein R¹ together with the carbon to which it is attached and the alpha-nitrogen and alpha-carbonyl represents an amino acid residue selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine.

Paragraph 3 in one aspect there is provided a compound of formula (I) according to paragraph 2, wherein R¹ together with the carbon to which it is attached and the alpha-nitrogen and alpha-carbonyl represents phenylalanine, valine, leucine or isoleucine.

Paragraph 4 in one aspect there is provided a compound of formula (I) according to paragraph 3, wherein in R¹ together with the carbon to which it is attached and the alpha-nitrogen and alpha-carbonyl represents valine, leucine or isoleucine.

Paragraph 5 in one aspect there is provided a compound of formula (I) according to any one of paragraphs 1 to 4, wherein R² together with the carbon to which it is attached and the alpha-nitrogen and alpha-carbonyl represents an amino acid residue selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine.

Paragraph 6 in one aspect there is provided a compound of formula (I) according to paragraph 5, wherein R² together with the carbon to which it is attached and the alpha-nitrogen and alpha-carbonyl represents phenylalanine, valine, leucine or isoleucine.

Paragraph 7 in one aspect there is provided a compound of formula (I) according to paragraph 6, wherein R² together with the carbon to which it is attached and the alpha-nitrogen and alpha-carbonyl represents valine, leucine or isoleucine.

Paragraph 8 in one aspect there is provided a compound of formula (I) according to any one of paragraph 1 to 7, wherein X represents a bond.

Paragraph 9 in one aspect there is provided a compound of formula (I) according to any one of paragraph 1 to 7, wherein X represents an amino acid residue selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine.

Paragraph 10 in one aspect there is provided a compound of formula (I) according to paragraph 9, wherein X represents arginine.

Paragraph 11 in one aspect there is provided a compound of formula (I) according to any one of claims 1 to 10, wherein R³ represents H.

Paragraph 12 in one aspect there is provided a compound of formula (I) according to any one of paragraph 1 to 10, wherein R³ represents methyl, ethyl, propyl or butyl.

Paragraph 13 in one aspect there is provided a compound of formula (I) according to any one of paragraph 1 to 12, wherein R⁴ represents H.

Paragraph 14 in one aspect there is provided a compound of formula (I) according to any one of paragraph 1 to 12, wherein R⁴ represents methyl, ethyl, propyl or butyl.

Paragraph 15 in one aspect there is provided a compound of formula (I) according to any one of paragraph 1 to 12, wherein R⁴ represents —R$^A$-L-Ar¹.

Paragraph 16 in one aspect there is provided a compound of formula (I) according to any one of paragraph 1 to 12, wherein R³ and R⁴ together with the nitrogen to which they are attached form a 5 or 6 membered heterocyclic group optionally including a further heteroatom selected from N, O and S.

Paragraph 17 in one aspect there is provided a compound of formula (I) according to paragraph 16, wherein the heterocyclic group is selected from pyrrolidine, piperidine, piperazine.

Paragraph 18 in one aspect there is provided a compound according to paragraph 17, wherein the compound has a formula (III) as defined above, wherein R¹, R², Z, YAr¹ and p are as defined above for compounds of formula (I).

Paragraph 19 in one aspect there is provided a compound of formula (I) according to paragraph 15, wherein R$^A$ is a bond.

Paragraph 20 in one aspect there is provided a compound of formula (I) according to paragraph 15, wherein R$^A$ represents —C$_{0-9}$ alkylC$_{6-10}$ aryl.

Paragraph 21 in one aspect there is provided a compound of formula (I) according to paragraph 20, wherein —C$_{6-10}$ aryl is phenyl or naphthyl.

Paragraph 22 in one aspect there is provided a compound of formula (I) according to paragraph 15, wherein R$^A$ represents —C$_{0-9}$ alkylC$_{5-11}$heteroaryl.

Paragraph 23 in one aspect there is provided a compound of formula (I) according to paragraph 15, wherein R$^A$ represents —C$_{0-9}$ alkylC$_{5-11}$ heterocycle.

Paragraph 24 in one aspect there is provided a compound of formula (I) according to paragraph 15, wherein R$^A$ represents C$_{0-9}$ alkylC$_{3-6}$cycloalkyl.

Paragraph 25 in one aspect there is provided a compound according to paragraph 15 wherein the compound has a formula (IV), as defined above, wherein R¹, R², R³, Z, L and Ar¹ are defined above for compounds of formula (I).

Paragraph 26 in one aspect there is provided a compound of formula (I) according to any one of paragraphs 15 and 19 to 25, wherein L represents C₀.

Paragraph 27 in one aspect there is provided a compound of formula (I) according to any one of paragraphs 15 and 19 to 25, wherein L represents a straight or branched C$_{1-9}$ alkyl chain wherein optionally one or more, such as one, carbon(s) is/are replaced by a heteroatom selected from O, N and S.

Paragraph 28 in one aspect there is provide a compound of formula (I) according to paragraphs 15 and 19 to 25 wherein L represents —$(CH_2)_2NH(CH_2)_j$ wherein i is an integer 1 to 12, j is 0 or 1, such as —$(CH_2)_3NHCH_2$—.

Paragraph 29 in one aspect there is provided a compound of formula (I) according to paragraph 16, 17 or 18, wherein Y represents $C_0$.

Paragraph 30 in one aspect there is provided a compound of formula (I) according to paragraph 16, 17 or 18, wherein Y represent a straight or branched $C_{1-5}$ alkyl chain wherein optionally one or more, such as one, carbon(s) is/are replaced by a heteroatom selected from O, N and S and a carbon in the chain is optionally substituted by oxo.

Paragraph 31 in one aspect there is provided a compound of formula (I) according to paragraph 30, wherein Y represent —$CH_2$— or —$CH_2CH_2NHC(O)$—.

Paragraph 32 in one aspect there is provided a compound of formula (I) according to any one of paragraphs 15 to 31, wherein $Ar^1$ represents phenyl substituted by 1, 2, 3, 4, or 5 halogen groups.

Paragraph 33 in one aspect there is provided a compound of formula (I) according to paragraph 32, wherein the halogen groups are selected from mono or di-fluoro, mono- or di-chloro and di-bromo.

Paragraph 34 in one aspect there is provided a compound of formula (I) according to paragraph 33, wherein the groups are selected from 4-chloro, 3,5-di-chloro, 3,4-di-chloro, 2,4-di-chloro and 2,4-di-fluoro.

Paragraph 35 in one aspect there is provided a compound of formula (I) according any one of paragraph 32 to 34, wherein —$NR^3R^4$ represents -piperazinyl$(CH_2)_n$phenyl, wherein n represents 0 or 1, or -piperazinyl$CH_2CH_2NHC$ (O)phenyl substituted by said halogen group(s).

Paragraph 36 in one aspect there is provided a compound of formula (I) according to any one of paragraph 15 to 31, wherein $Ar^1$ represents phenyl substituted by one or two nitro groups.

Paragraph 37 in one aspect there is provided a compound of formula (I) according to paragraph 36, wherein the nitro groups are selected from 4-nitro, 3,5-di-nitro, 3,4-di-nitro and 2,4-di-nitro.

Paragraph 38 in one aspect there is provided a compound of formula (I) according to paragraph 36 or 37, wherein —$NR^3R^4$ represents -piperazinyl$(CH_2)_n$phenyl, wherein n represents 0 or 1, or -piperazinyl$CH_2CH_2NHC(O)$phenyl substituted by said nitro group(s).

Paragraph 39 in one aspect there is provided a compound of formula (I) according to any one of paragraphs 1 to 38, wherein $R^5$ represents an amino acid residue, for example selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine.

Paragraph 40 in one aspect there is provided a compound of formula (I) according to paragraph 39, wherein $R^5$ represents phenylalanine, valine, leucine or isoleucine.

Paragraph 41 in one aspect there is provided a compound of formula (I) according to any one of paragraphs 1 to 40, wherein Z represents H.

Paragraph 42 in one aspect there is provided a compound of formula (I) according to any one of paragraphs 1 to 40, wherein Z represents methyl, ethyl, propyl or butyl.

Paragraph 43 in one aspect there is provided a compound of formula (I) according to any one of paragraphs 1 to 40, wherein Z represents an amino acid residue selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine.

Paragraph 44 in one aspect there is provided a compound of formula (I) according to paragraph 43, wherein the amino acid is alanine or serine.

Paragraph 45 in one aspect there is provided a compound of formula (I) according to any one of paragraph 1 to 40, wherein Z represents —$R^B$-Q-$Ar^2$.

Paragraph 46 in one aspect there is provided a compound of formula (I) according to paragraph 45 wherein $R^B$ represents a bond.

Paragraph 47 in one aspect there is provided a compound of formula (I) according to paragraph 45 wherein $R^B$ represents $C_{0-9}$ alkyl$C_{6-10}$aryl.

Paragraph 48 in one aspect there is provided a compound of formula (I) according to paragraph 47, wherein $C_{6-10}$ aryl is phenyl.

Paragraph 49 in one aspect there is provided a compound of formula (I) according to paragraph 45 wherein $R^B$ represents —$C_{0-9}$ alkyl$C_{5-10}$heteroaryl, Paragraph 50 in one aspect there is provided a compound of formula (I) according to paragraph 45 wherein $R^B$ represents —$C_{0-9}$ alkyl$C_{3-6}$cycloalkyl, Paragraph 51 in one aspect there is provided a compound of formula (I) according to paragraph 45 wherein $R^B$ represents $C_{0-9}$ alkyl$C_{5-11}$ heterocycle.

Paragraph 52 in one aspect there is provided a compound of formula (I) according to any one of paragraph 45 to 51 wherein Q represents $C_0$.

Paragraph 53 in one aspect there is provided a compound of formula (I) according to any one of paragraph 45 to 51 wherein Q represents a straight or branched, such as straight, $C_{1-9}$ alkyl chain wherein optionally one or more, such as one, carbon(s) is/are replaced by a heteroatom selected from O, N and S.

Paragraph 54 in one aspect there is provided a compound of formula (I) according to any one of paragraph 45 to 53 wherein $Ar^2$ is phenyl substituted by 1, 2, 3, 4, or 5 halogen groups.

Paragraph 55 in one aspect there is provided a compound of formula (I) according to any one of paragraph 45 to 53 wherein $Ar^e$ represents phenyl substituted by one or two nitro groups.

Paragraph 56 in one aspect there is provided a compound of formula (I) according to any one of paragraph 1 to 55, wherein p represents 0

Paragraph 57 in one aspect there is provided compound of formula (I) according to any one of paragraph 1 to 55, wherein p represents 1.

Paragraph 58 in one aspect there is provided a compound of formula (I) according to any one of paragraph 1 to 57, wherein the fragment:

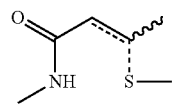

represents:

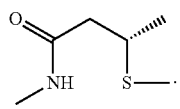

Paragraph 59 there is also provided a pharmaceutical composition comprising a compound of formula (I) as per any one of paragraphs 1 to 58 and a pharmaceutically acceptable excipient.

Paragraph 60 in one aspect there is provided a compound as defined in any one of paragraph 1 to 58 or a composition as defined in paragraph 59, for use in treatment.

Paragraph 61 one aspect there is provided a compound as defined in any one of paragraph 1 to 58 or a composition as defined in paragraph 59, for use as an antimicrobial agent.

Paragraph 62 there is also provided a compound or composition according to paragraph 60 or 61, for use in the treatment of the microbial infection, such as *Staph. aureus* including MRSA, *E. faecalis, E. faecium, S. pyogenes, Streptococcus pneumoniae* and/or *C. difficile*.

Paragraph 63 in one aspect there is provided a method of treatment comprising administering a therapeutically effective amount of a compound as defined in any one of paragraph 1 to 58 or a composition as defined in paragraph 59, to a patient in need thereof.

Paragraph 64 in one aspect there is provided a method of treatment according to paragraph 63, the treatment of the microbial infection *S. aureus* infection such as MRSA, *E. faecalis, S. pyogenes, Streptococcus pneumoniae* and/or *C. difficile*.

In one embodiment there is provided a compounds of formula (II):

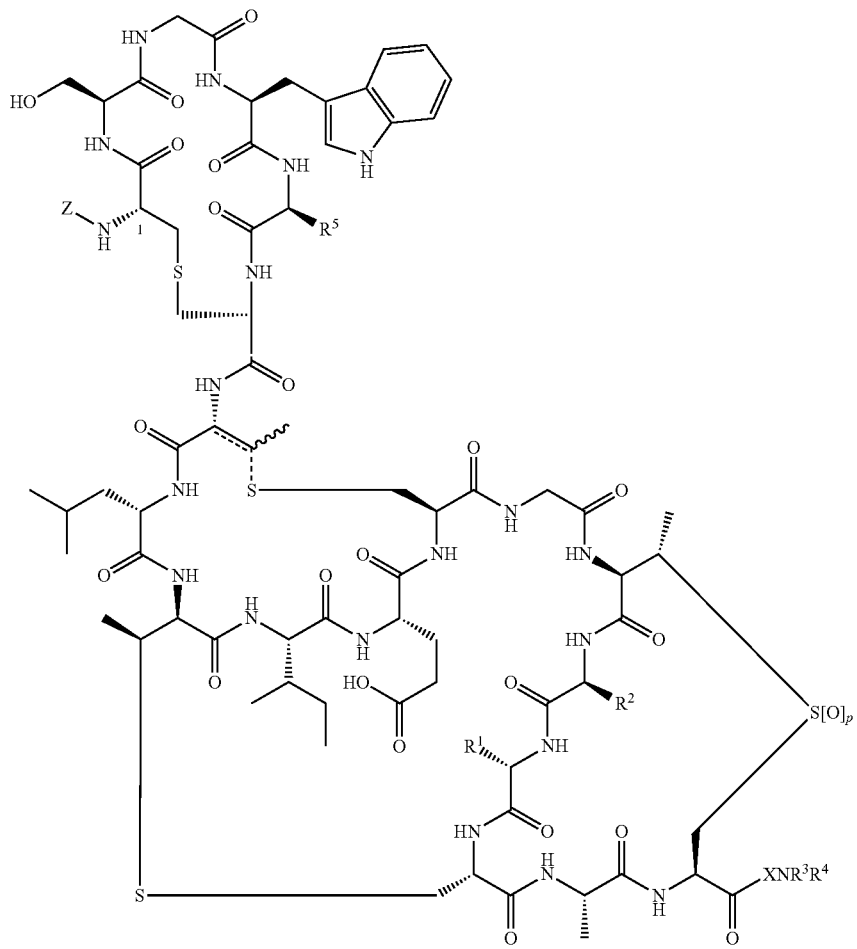

(II)

wherein $R^1$, $R^2$, $R^3$, $R^4$, $R^5$ and p are defined above for compounds of formula (I), and Z is H, $C_{1-6}$ alkyl or an amino acid, for example where Z is H or ala, in particular H.

In one embodiment $Ar^1$ represents phenyl substituted by one or two $NO_2$ groups or one to five such as 2, 3, or 4 halogen groups, or a combination thereof In one embodiment of compounds of formula (II) there is provided a compound is of formula (III) wherein —$XNR^3R^4$ is piperazine-$YAr^1$.

In one embodiment of compounds of formula (II) or (III) Y is $C_0$.

In one embodiment of compounds of formula (II) or (III) Y is —$CH_2$—.

In one embodiment of compounds of formula (II) or (III) Y is $C_{2-12}$ alkyl chain wherein optionally one or more carbons (for example 1 to 3, such as 2) are replaced by a heteroatom independently selected from N, O or S, wherein said chain is optionally substituted by one or more (for example 1 or 2), oxo or nitro groups, such as wherein Y is —CH$_2$CH$_2$NHC(O)—, —CH$_2$CH$_2$CH$_2$NHC(O)— or —CH$_2$CH$_2$NHCH$_2$—, in particular wherein Y is —CH$_2$CH$_2$NHC(O)—, —CH$_2$CH$_2$NHCH$_2$—.

In one embodiment —XNR$^3$R$^4$ is not piperazine substituted in position 4 by benzyl bearing 1 or 2 substituents selected from chloro, bromo or fluoro.

In one embodiment the compound of formula (II) is a compound of formula (IV):

6 membered heterocyclic group optionally including a further heteroatom selected from N, O or S, wherein said heterocyclic group is substituted by YAr$^1$;

R$^A$ represents a bond, —C$_{0-9}$ alkylC$_{6-10}$aryl, —C$_{0-9}$ alkyl C$_{5-11}$heteroaryl, —C$_{0-9}$ alkylC$_{3-6}$cycloalkyl, or —C$_{0-9}$ alkylC$_{5-11}$ heterocycle;

L represents a straight or branched C$_{0-15}$ alkyl chain wherein optionally one or more carbons are replaced by a heteroatom independently selected from N, O or S, wherein said chain is optionally substituted by one or more, oxo or nitro groups with the proviso that a heteroatom is not bonded directly to the N of the group —NR$^3$R$^4$;

(IV)

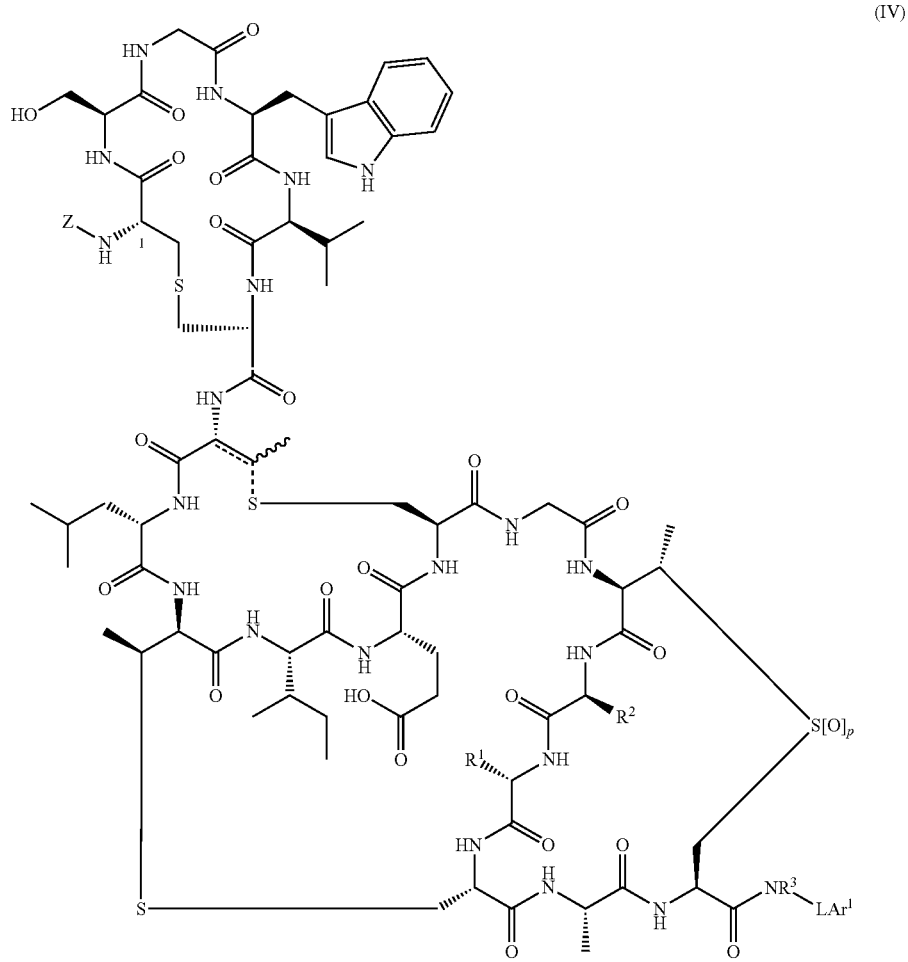

wherein R$^1$, R$^2$, R$^3$, L and Ar$^1$ are defined above for compounds of formula (II) and Z is H, C$_{1-6}$ alkyl or an amino acid, for example where Z is H or ala, in particular H.

In one embodiment of compounds of formula (II) or (IV) then:

R$^1$ together with the carbon to which it is attached and the alpha-nitrogen and alpha-carbonyl represents an amino acid residue;

R$^2$ together with the carbon to which it is attached and the alpha-nitrogen and alpha-carbonyl represents an amino acid residue;

X represents a bond or an amino acid residue;

R$^3$ represents H or C$_{1-6}$ alkyl;

R$^4$ represents H, C$_{1-6}$ alkyl, —R$^A$-L-Ar$^1$, or R$^3$ together with R$^4$ and the nitrogen to which they are attached form a 5 or Y represents a straight or branched C$_{0-15}$ alkyl chain wherein optionally one or more carbons are replaced by a heteroatom independently selected from N, O or S, wherein said chain is optionally substituted by one or more, oxo or nitro groups;

Ar$^1$ represents phenyl substituted by one or two NO$_2$ groups or one to five such as 2, 3, or 4 halogen groups, or one or two C$_{1-3}$ haloalkyl groups, or a combination thereof;

R$^5$ together with the carbon to which it is attached and the alpha-nitrogen and alpha-carbonyl represents an amino acid residue:

Z represents H, C$_{1-6}$ alkyl, an amino acid residue;

p represents 0 or 1; and the fragment:

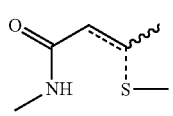

represents:

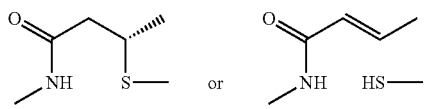

or the E isomer of the latter,
or a pharmaceutically acceptable salt thereof.

In certain embodiments of compounds of formula (II) or (IV) $R^A$ represents a bond, —$C_{0-9}$ alkyl$C_{5-11}$heteroaryl, —$C_{0-9}$ alkyl$C_{3-6}$cycloalkyl, or —$C_{0-9}$ alkyl$C_{5-11}$ heterocycle.

In certain embodiments of compounds of formula (II), (III) or (IV) $Ar^1$ is di-nitrophenyl or di-halophenyl, for example:
3,5-di-chlorophenyl, 3,4-di-chlorophenyl, 2,4-di-chlorophenyl, 3,5-di-fluorophenyl, 3,4-di-fluorophenyl or 2,4-di-fluorophenyl, or
3,5-di-nitrophenyl, 3,4-di-nitrophenyl or 2,4-di-nitrophenyl.

In certain embodiments of compounds of formula (II), (III) or (IV) L represents $C_0$.

In certain embodiments of compounds of formula (II), (III) or (IV) L represents a straight or branched $C_{1-9}$ alkyl chain wherein optionally one or more, such as one, carbon(s) is/are replaced by a heteroatom selected from O, N and S, for example L is a straight alkyl chain.

In certain embodiments of compounds of formula (II), (III) or (IV) L represents —$(CH_2)_iNH(CH_2)_j$ wherein i is an integer 1 to 12, j is 0 or 1, for example selected from —$(CH_2)_2NHCH_2$—, —$(CH_2)_3NHCH_2$—, —$(CH_2)_4NHCH_2$—, —$(CH_2)_5NHCH_2$—, —$(CH_2)_6NHCH_2$—, —$(CH_2)_7NHCH_2$— and —$(CH_2)_5NHCH_2$—.

In certain embodiments of compounds of formula (II), (III) or (IV) L represents a straight $C_{1-15}$ alkyl chain wherein optionally one or two carbons are replaced by a heteroatom independently selected from N, O or S, wherein said chain is optionally substituted by one or two, oxo groups, for example selected from —$(CH_2)_3NHCO$—, —$(CH_2)_3NH(CH_2)_3NHCH_2$— and —$(CH_2)_7NHSO_2$—.

In one embodiment the compound of formula (I) or (II) is selected from:
Deoxyactagardine B (3,5-dichlorobenzylamine)monocarboxamide;
Actagardine (3,5-dichlorobenzylamine)monocarboxamide;
Deoxyactagardine B 19-[4-(4'-nitrophenyl)piperazine]monocarboxamide;
Deoxyactagardine B 19-[4-(4'-chlorophenyl)piperazine]monocarboxamide;
Deoxyactagardine B [2,4-dichlorobenzylamine]monocarboxamide;
Deoxyactagardine B [4-(3',5'-dichlorobenzyl)piperazine]monocarboxamide;
Deoxyactagardine B [4-(2'-fluoro-4'-bromobenzyl)-piperazine]monocarboxamide;
Deoxyactagardine B [4-(4'-nitrobenzyl)piperazine]monocarboxamide;
Deoxyactagardine B [4-bromobenzylamine]monocarboxamide;
Deoxyactagardine B [4-(3',4'-dichlorophenyl)piperazine]monocarboxamide;
Deoxyactagardine B [3-(3',5'-dichlorobenzylamino)-1-propylamine]monocarboxamide;
Deoxyactagardine B [7-(3',5'-dichlorobenzylamino)-1-heptylamine]monocarboxamide;
Deoxyactagardine B [4-(2'-(3",5"-dichlorobenzylamino)ethyl)-piperazine]monocarboxamide;
Deoxyactagardine B [1-(4-chlorophenyl)piperazine]monocarboxamide;
Deoxyactagardine B (2,4-difluorobenzylamine)monocarboxamide;
Deoxyactagardine B 19-[4-(2'-(3",5"-dinitrobenzamido)-ethyl)-piperazine]monocarboxamide;
V15F Actagardine (3,5-dichlorobenzylamine)monocarboxamide;
Deoxyactagardine B [3-(3',5'-dichlorobenzamido)-propylamine]monocarboxamide;
Deoxyactagardine B 19-[4-(3',5'-dichlorobenzylaminomethyl)-benzyl]monocarboxamide;
Deoxyactagardine B [3-(3'-(3",5"-dichlorobenzylamino)-propylamino)propylamine]monocarboxamide;
Deoxyactagardine B (2,5-dichlorobenzylamine)monocarboxamide;
Deoxyactagardine B (3,4-dichlorobenzylamine)monocarboxamide;
Deoxyactagardine B (2-chlorobenzylamine)monocarboxamide;
Deoxyactagardine B (3-chlorobenzylamine)monocarboxamide;
Deoxyactagardine B (4-chlorobenzylamine)monocarboxamide;
Deoxyactagardine B (2,6-dichlorobenzylamine)monocarboxamide;
Deoxyactagardine B [6-(2',4',6'-trichlorobenzenesulfonamido)-hexylamine]monocarboxamide;
Deoxyactagardine B [5-(3',5'-dichlorobenzylamino)-pentylamine]monocarboxamide;
Deoxyactagardine B [2-(3',5'-dichlorobenzylamino)ethylamine]monocarboxamide;
Deoxyactagardine B [6-(3',5'-dichlorobenzylamino)-hexylamine]monocarboxamide;
Deoxyactagardine B [8-(3',5'-dichlorobenzylamino)-octylamine]monocarboxamide;
Deoxyactagardine B [3-(2'-aminomethyl-4'-(2",4"-dichlorophenyl)-furanyl)propylamine]monocarboxamide; and
Deoxyactagardine B [3-(2'-aminomethyl-4'-(2"-nitro-4"-chlorophenyl)-furanyl)propylamine]monocarboxamide.

In one embodiment there is provided a process of preparing a compound of formula (II) by reacting a compound of formula (Ia):

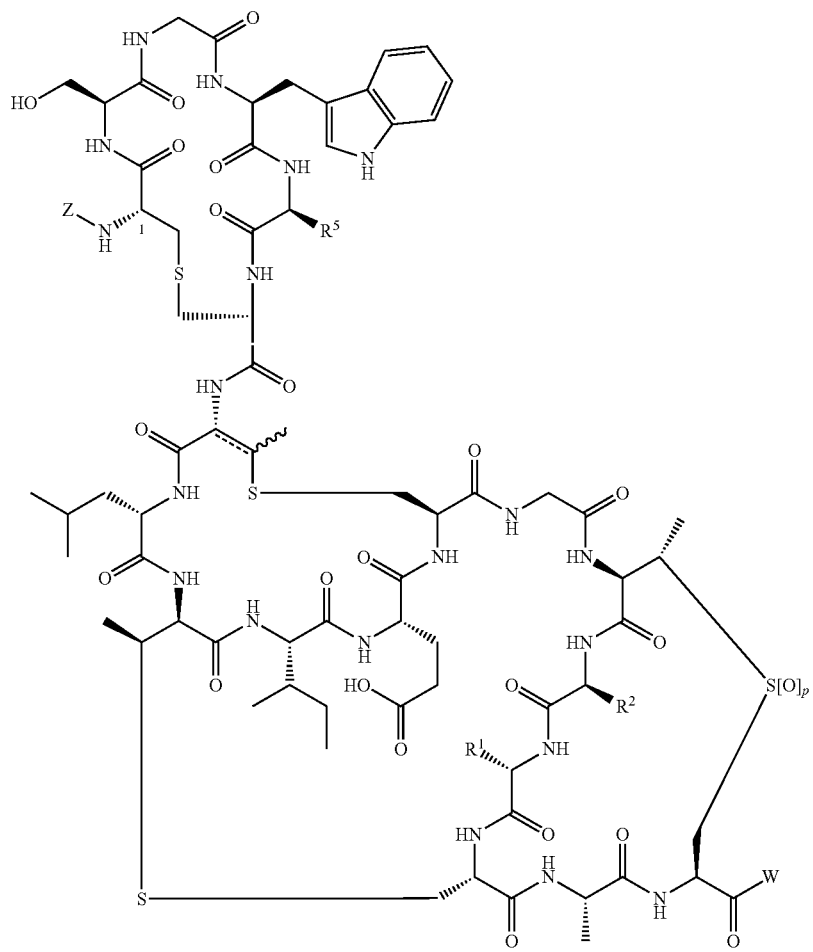

(Ia)

wherein:

R[1] together with the carbon to which it is attached and the alpha-nitrogen and alpha-carbonyl represents an amino acid residue;

R[2] together with the carbon to which it is attached and the alpha-nitrogen and alpha-carbonyl represents an amino acid residue;

W represents —OH or an amino acid with an unreacted C-terminal;

R[5] together with the carbon to which it is attached and the alpha-nitrogen and alpha-carbonyl represents an amino acid residue:

Z represents H, $C_{1-6}$ alkyl, an amino acid residue;

p represents 0 or 1;

and the fragment

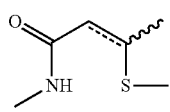

represents:

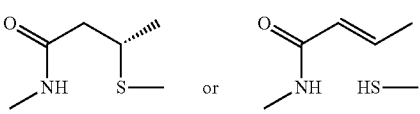

or the E isomer of the latter,
with group NHR[3]R[4].

The compounds of the present disclosure may be in the form of and/or may be administered as a pharmaceutically acceptable salt. For a review on suitable salts see Berge et al., J. Pharm. ScL, 1977, 66, 1-19.

Typically, a pharmaceutically acceptable salt may be readily prepared by using a desired acid or base as appropriate. The salt may precipitate from solution and be collected by filtration or may be recovered by evaporation of the solvent, for example, a compound of formula (I) may be dissolved in a suitable solvent, for example an alcohol such as methanol, and the acid may be added in the same solvent or another suitable solvent. The resulting acid addition salt may then be precipitated directly, or by addition of a less polar solvent such as diisopropyl ether or hexane, and isolated by filtration.

The skilled person will appreciate that where the compound of formula (I) contains more than one basic group bis salts or tris salts may also be formed and are salts according to the present disclosure.

Suitable addition salts are formed from inorganic or organic acids which form non-toxic salts and examples are lactobionate, mandelate (including (S)-(+)-mandelate, (R)-(−)-mandelate and (R,S)-mandelate), hydrochloride, hydrobromide, hydroiodide, sulfate, bisulfate, nitrate, phosphate, hydrogen phosphate, glutamate, acetate, trifluoroacetate, maleate, malate, fumarate, lactate, tartrate, citrate, formate, gluconate, succinate, ethyl succinate (4-ethoxy-4-oxo-butanoate), pyruvate, oxalate, oxaloacetate, saccharate, benzoate, glucolate, glucurinate, alkyl or aryl sulphonates (eg methanesulphonate, ethanesulphonate, benzenesulphonate or p-toluenesulphonate), mesylate and isethionate.

Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Salts may be employed to optimize the solubility of the compounds of the present disclosure.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of formula (I) are within the scope of the disclosure. The salts of the compound of the disclosure may form solvates (e.g. hydrates) and the disclosure also includes all such solvates.

The term "prodrug" as used herein means a compound which is converted within the body, e.g. by hydrolysis in the blood, into its active form that has medical effects. Pharmaceutically acceptable prodrugs are described in T. Higuchi and V. Stella, "Prodrugs as Novel Delivery Systems", Vol. 14 of the A.C.S. Symposium Series; Edward B. Roche, ed., "Bioreversible Carriers in Drug Design", American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of formula (I), (II), (III) or (IV) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of formula (I), (II), (III) or (IV). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

References hereinafter to a compound according to the disclosure include both compounds of formula (I), (II), (III) or (IV) and their pharmaceutically acceptable salts and derivatives. Unless the context specifically indicates otherwise references to compounds of formula (I) includes other compounds within scope of the present invention.

With regard to stereoisomers, the compounds of formula (I), (Ia), (II), (III) and (IV) have more than one asymmetric carbon atom. In the general formula (I), (II), (III) or (IV) as drawn, the solid wedge shaped bond indicates that the bond is above the plane of the paper. The broken bond indicates that the bond is below the plane of the paper.

It will be appreciated that the substituents in compounds of formula (I), (Ia), (II), (III) or (IV) may also have one or more asymmetric carbon atoms.

The compounds of structure (I), (II), (III) or (IV) may occur as individual enantiomers or diastereomers. All such isomeric forms are included within the present disclosure, including mixtures thereof.

Separation of diastereoisomers or cis and trans isomers may be achieved by conventional techniques, e.g. by fractional crystallisation, chromatography or HPLC. A stereoisomeric mixture of the agent may also be prepared from a corresponding optically pure intermediate or by resolution, such as by HPLC, of the corresponding mixture using a suitable chiral support or by fractional crystallisation of the diastereoisomeric salts formed by reaction of the corresponding mixture with a suitable optically active acid or base, as appropriate. Compounds of formula (I), (II), (III) or (IV) as described herein also extend to tautomeric forms thereof, for example, keto/enol tautomers.

The compounds of formula (I), (II), (III) or (IV) may be in crystalline or amorphous form. Furthermore, some of the crystalline forms of the compounds of structure (I), (II), (III) or (IV) may exist as polymorphs, all forms which are included in the present disclosure.

In another aspect, the invention provides a pharmaceutical composition comprising, as active ingredient, a compound of the disclosure or a pharmaceutically acceptable derivative thereof in association with a pharmaceutically acceptable excipient, diluent and/or carrier for use in therapy, and in particular, in the treatment of human or animal subjects suffering from a condition susceptible to amelioration by an antimicrobial compound.

In another aspect, the invention provides a pharmaceutical composition comprising a therapeutically effective amount of a compound of the present disclosure and a pharmaceutically acceptable excipient, diluent and/or carrier (including combinations thereof).

There is further provided by the present disclosure a process of preparing a pharmaceutical composition, which process comprises mixing a compound of the disclosure or a pharmaceutically acceptable derivative thereof, together with a pharmaceutically acceptable excipient, diluent and/or carrier.

The compounds of the disclosure may be formulated for administration in any convenient way for use in human or veterinary medicine and the disclosure therefore includes within its scope pharmaceutical compositions comprising a compound of the disclosure adapted for use in human or veterinary medicine. Such compositions may be presented for use in a conventional manner with the aid of one or more suitable excipients, diluents and/or carriers. Acceptable excipients, diluents and carriers for therapeutic use are well known in the pharmaceutical art, and are described, for example, in Remington's Pharmaceutical Sciences, Mack Publishing Co. (A. R. Gennaro edit. 1985). The choice of pharmaceutical excipient, diluent and/or carrier can be selected with regard to the intended route of administration and standard pharmaceutical practice. The pharmaceutical compositions may comprise as—or in addition to—the excipient, diluent and/or carrier any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

For some embodiments, the agents of the present disclosure may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e. g. as a carrier, diluent or solubiliser. Alpha-, beta- and gamma-cyclodextrins are most commonly used and suitable examples are described in WO 91/11172, WO 94/02518 and WO 98/55148.

The compounds of the disclosure may be milled using known milling procedures such as wet milling to obtain a particle size appropriate for tablet formation and for other formulation types. Finely divided (nanoparticulate) preparations of the compounds of the invention may be prepared by processes known in the art, for example see International Patent Application No. WO 02/00196 (SmithKline Beecham).

The routes for administration (delivery) include, but are not limited to, one or more of: oral (e. g. as a dry powder/free flowing particulate formulation, tablet, capsule, or as an ingestable solution or suspension) rectal, buccal, and sublingual. The compositions of the disclosure include those in a form especially formulated for parenteral, oral, buccal, rectal, topical, implant, ophthalmic, nasal or genito-urinary use. In one aspect of the invention, the agents are delivered orally, hence, the agent is in a form that is suitable for oral delivery.

In some instances it may be possible to deliver the compounds of the disclosure by a topical, parenteral (e. g. by an injectable form) or transdermal route, including mucosal (e. g. as a nasal spray or aerosol for inhalation), nasal, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral).

There may be different composition/formulation requirements depending on the different delivery systems. By way of example, the pharmaceutical composition of the present disclosure may be formulated to be delivered using a mini-pump or by a mucosal route, for example, as a nasal spray or aerosol for inhalation or ingestable solution, or parenterally in which the composition is formulated in an injectable form, for delivery by, for example, an intravenous, intramuscular or subcutaneous route. Alternatively, the formulation may be designed to be delivered by both routes. Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously.

For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner. If a compound of the present disclosure is administered parenterally, then examples of such administration include one or more of: intravenously, intraarterially, intraperitoneally, intrathecally, intraventricularly, intraurethrally, intrasternally, intracranially, intramuscularly or subcutaneously administering the agent, and/or by using infusion techniques.

The compounds of the disclosure can be administered (e. g. orally or topically) in the form of tablets, capsules, ovules, elixirs, solutions or suspensions, which may contain flavouring or colouring agents, for immediate-, delayed-, modified-, sustained-, pulsed- or controlled-release applications.

The compounds of the disclosure may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents.

Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, calcium sulphate, dibasic calcium phosphate and glycine, mannitol, pregelatinised starch, corn starch, potato starch, disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

Solid compositions of a similar type may also be employed as fillers in gelatin or HPMC (hydroxypropyl methylcellulose) capsules. Preferred excipients in this regard include microcrystalline cellulose, lactose, calcium carbonate, calcium sulphate, dibasic calcium phosphate and, mannitol, pregelatinised starch, corn starch, potato starch or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

Capsules, may be filled with a powder (of medicament alone or as blend with selected filler(s)) or alternatively a liquid, each comprising one or more compounds of formula (I) and a carrier. Where the capsule is filled with a powder the compounds of formula (I) and/or the carrier may be milled or micronised to provide material with an appropriate particle size.

Compounds of the disclosure may be coated, for example with as an enteric coating when administered orally as a tablet or capsule. The tablet or capsule, as appropriate, may, for example be coated by a thin film such as a EUDRAGIT® film available from Rohm Pharma Polymers, which allows controlled dissolution in the gastrointestinal tract. The films are available as cationic polymers such as EUDRAGIT® E 100 (aminoalkyl methacylate copolymers) or as anionic acrylic polymers such as EUDRAGIT® L (methacrylic acid copolymers) and EUDRAGIT S.

Permeable acrylic polymers such as EUDRAGIT® RL (amino methacrylate copolymer) and EUDRAGIT® RS are also available.

These coating formulations may be prepared as an aqueous dispersion including optional ingredients such as talc, silicone antifoam emulsion, polyethylene glycol. Alternatively the coating formulation may be prepared as an organic polymer solution.

Alternatively, tablets may be coated using OPADRY® (Surelease®) coating systems, available from Colorcon. Aqueous systems generally comprise up to 15% w/w of OPADRY®. Organic solvent systems generally comprise up to 5% w/w of OPADRY®.

The coatings may be prepared by known techniques, for example by;
1. weighing the required quantity of OPADRY® film coating system, 2. weighing the required quantity of water or other solvent(s) into a mixing vessel, 3. with a mixing propeller in the centre of the vessel and as close to the bottom of the vessel as possible, stirring the solvents to form a vortex without drawing air into the liquid, 4. steadily and quickly adding the OPADRY® powder to the vortex, avoiding powder flotation on the liquid surface, 5. increasing the stirrer speed in order to maintain the vortex, if required, and 6. after all the powder ingredients have been added, reducing the mixer speed and continuing mixing for approximately 45 minutes.

Coatings can be applied by known techniques, using tablet coating machines.

The thickness of the coating applied is generally in the range 5 to 35 microns such as 10 to 30 microns, more specifically 10 or 20 microns, depending on the required effect.

Alternatively, the tablet or a capsule, as appropriate, may be filled into another capsule (preferably a HPMC capsule such as Capsugel®) to provide either a tablet in capsule or capsule in capsule configuration, which when administered to a patient yields controlled dissolution in the gastrointestinal tract thereby providing a similar effect to an enteric coating.

Thus in one aspect the disclosure provides a solid dose formulation of a compound of formula (I), (II), (III) or (IV), for example where the formulation has an enteric coating.

In another aspect the disclosure provides a solid dose formulation comprising a protective capsule as outer layer, for example as a tablet in a capsule or a capsule in a capsule. The enteric coating may provide an improved stability profile over uncoated formulations.

Having said this it is believed that the compounds of formula (I) are not particularly susceptible to degradation by stomach acid or intestinal enzymes in vivo.

The compounds of the disclosure may also be administered orally, in veterinary medicine, in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

In one embodiment the formulation is provided as a formulation for topical administration including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are preferably used, the use of lactose or glucose, particularly but not exclusively in the form of their hydrates.

Particles for deposition in the lung require a particle size less than 10 microns, such as 1-9 microns suitably from 0.1 to 5 µm, particularly preferably from 1 to 5 µm. The particle size of the active (i.e. the compound according to the disclosure).

The propellent gases which can be used to prepare the inhalable aerosols are known from the prior art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The above-mentioned propellent gases may be used on their own or in mixtures thereof.

Particularly suitable propellent gases are halogenated alkane derivatives selected from among TG11, TG 12, TG 134a and TG227. Of the abovementioned halogenated hydrocarbons, TG134a (1,1,1,2-tetrafluoroethane) and TG227 (1,1,1,2,3,3,3-heptafluoro propane) and mixtures thereof are suitable for use in formulations of the present invention.

The propellant-gas-containing inhalable aerosols may also contain other ingredients such as co-solvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the disclosure may contain, for example, 0.002 to 5% by weight, 0.01 to 3% by weight, 0.015 to 2% by weight, 0.1 to 2% by weight, 0.5 to 2% by weight or 0.5 to 1% by weight of active.

The compounds of the disclosure may also be used in combination with other therapeutic agents. The disclosure thus provides, in a further aspect, a combination comprising a compound of formula (I), (II), (III) or (IV) or a pharmaceutically acceptable derivative thereof together with a further therapeutic agent. The combination may, for example be a combination of a compound of formula (I), (II), (III) or (IV) and an antibiotic, such as vancomycin, a beta-lactam (such as a cephalosporin), an aminoglycoside, a macrolide, a tetracyline, a lipopeptide, an oxazolidinone and/or an anti-inflammatory such as a steriod. The combination may be provided as a co-formulation or simply packaged together as separate formulations, for simultaneous or sequential delivery.

It is to be understood that not all of the compounds of the combination need be administered by the same route. Thus, if the therapy comprises more than one active component, then those components may be administered by different routes.

The individual components of such combinations may be administered either sequentially or simultaneously in separate or combined pharmaceutical formulations by any convenient route.

When administration is sequential, either the compound of the disclosure or the second therapeutic agent may be administered first. When administration is simultaneous, the combination may be administered either in the same or a different pharmaceutical composition.

The combinations referred to above may conveniently be presented for use in the form of a pharmaceutical formulation and thus pharmaceutical formulations comprising a combination as defined above together with a pharmaceutically acceptable carrier or excipient comprise a further aspect of the disclosure.

When combined in the same formulation it will be appreciated that the two compounds must be stable and compatible with each other and the other components of the formulation. When formulated separately they may be provided in any convenient formulation, in such manner as are known for such compounds in the art.

The compositions may contain from 0.01-99% of the active material. For topical administration, for example, the composition will generally contain from 0.01-10%, more preferably 0.01-1% of the active material.

When a compound of the disclosure or a pharmaceutically acceptable derivative thereof is used in combination with a second therapeutic agent active against the same disease state the dose of each compound may be the same or differ from that employed when the compound is used alone. Appropriate doses will be readily appreciated by those skilled in the art. It will also be appreciated that the amount of a compound of the disclosure required for use in treatment will vary with the nature of the condition being treated and the age and the condition of the patient and will be ultimately at the discretion of the attendant physician or veterinarian.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

For oral and parenteral administration to humans, the daily dosage level of the agent may be in single or divided doses. For systemic administration the daily dose as employed for adult human treatment it will range from 2-100 mg/Kg body weight, preferably 5-60 mg/Kg body weight, which may be administered in 1 to 4 daily doses, for example, depending on the route of administration and the condition of the patient. When the composition comprises dosage units, each unit will preferably contain 100 mg to 1 g of active ingredient. The duration of treatment will be dictated by the rate of response rather than by arbitrary numbers of days.

In one embodiment the treatment regime is continued for 1, 2, 3, 4, 5, 6, 7, 8, 9, 10, 11, 12, 13, 14, 15, 16, 17, 18, 19, 20, 21 or more days.

As described above, the compounds of the present disclosure may be employed in the treatment or prophylaxis of humans and/or animals.

In one embodiment a compound of formula (I), (II), (III) or (IV) is useful in the treatment of skin infections, in particular bacterial skin and soft tissue infection.

In one aspect, the disclosure provides use of a compound of formula (I), (II), (III) or (IV) in therapy, for example, for treatment of microbial infections such as bacteraemia, pneumonia and microbial infection of soft tissue including surgical wounds, in particular staphylococcal infections including MRSA infection.

In one embodiment the compounds of formula (I), (II), (III) or (IV) are useful for the treatment of enterococcal infections including *E. faecalis* and *E. faecium* infection, for example skin and skin structure infections, endocarditis, urinary tract infection and sepsis.

In one embodiment the compounds of formula (I), (II), (III) or (IV) are useful for the treatment of *S. pyogenes*, for example skin infections such as impetigo, erysipelas and cellulitis, throat infections, scarlet fever, and acute glomerulonephritis.

In one embodiment compounds of formula (I), (II), (III) or (IV) are useful in the treatment of *Streptococcus pneumoniae* infection, for example pnuemonia, acute sinusitus, otitis media, meningitis, bacteremia, osteomylitis, septic arthritis and endocarditis.

In one aspect the compounds of formula (I), (II), (III) or (IV) are employed for controlling bacterial overgrowth syndrome. Overgrowth syndrome (BOS) occurs when the normally low bacterial colonization in the upper GI tract and/or lower intestines significantly increases.

In one aspect, the disclosure provides use of a compound of formula (I), (II), (III) or (IV) in therapy, for example, for treatment of microbial infections such as *C. difficile* infection, in particular diarrhoea associated therewith, or one or more microbial infections described herein, particularly by oral delivery of a compound of formula (I), (II), (III) or (IV).

In one aspect there is provided use of a compound of formula (I), (II), (III) or (IV) for the prophylaxis, treatment or maintenance of IBS (irritable bowel syndrome). See for example Rifaximin Treatment for Symptoms of Irritable Bowel Syndrome. Andrea L. Fumi and Katherine Trexler, *The Annals of Pharmacotherap*, 2008, 4, 408.

In one embodiment a compound of formula (I) (II), (III) or (IV) is useful in the treatment of ulcerative colitis including prophylactic treatment to prevent recurrence thereof. The compounds may be particularly suitable for the treatment of steroid refractory ulcerative colitis. See for example steroid-refractory ulcerative colitis treated with corticosteroids, metronidazole and vancomycin: a case report J. Miner, M. M Gillan, P. Alex, M Centola, *BMC Gastroenterology* 2005, 5:3.

The compounds of the present disclosure are particularly useful for long term treatment.

In one aspect there is provided a compound of formula (I), (II), (III) or (IV) or a composition comprising same for use in treatment or prophylaxis for example the treatment or prophylaxis of any one the indications described herein.

In one aspect there is provided a compound of formula (I), (II), (III) or (IV) or a composition comprising the same for the manufacture of a medicament for one or more of the indications defined above.

In one aspect there is provided a method of treatment comprising the step of administering a therapeutically effective amount of a compound of formula (I), (II), (III) or (IV) or a pharmaceutical composition containing the same to a patient (human or animal) in need thereof, for example for the treatment of an infection/illness or disease as described herein.

In the context of this specification "comprising" is to be interpreted as "including".

Aspects of the invention comprising certain elements are also intended to extend to alternative embodiments "consisting" or "consisting essentially" of the relevant elements.

Where technically appropriate embodiments may be combined and thus the disclosure extends to all permutations/combinations of the embodiments provided herein.

Preferences given for compounds of formula (I) may equally apply to other compounds of the invention, disclosed herein, as technically appropriate.

EXAMPLES

In each of the examples below the entity shown is linked to the DAB or actagardine entity through the C terminus and therefore the specific substituents shown correspond to $XNR^3R^4$ in compounds of formula (I).

Example 1

Deoxyactagardine B
(3,5-dichlorobenzylamine)monocarboxamide

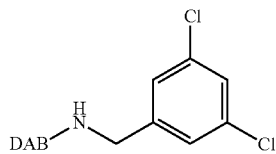

Deoxyactagardine B [DAB] (200 mg), 3,5-dichlorobenzylamine (38 mg) and diisopropylethylamine (35 µL) were dissolved in dry dimethylformamide (1 mL). A solution of benzotriazole-1-yl-oxy-tris-pyrrolidino-phosphonium hexafluorophosphate (PyBOP) (84 mg) in dry DMF (2 mL) was added portionwise. The reaction was followed by analytical hplc (See Table 1) and PyBOP was added until the starting material had been consumed (FIGS. 4 & 5).

TABLE 1

Analytical HPLC conditions for the separation of lantibiotic (e.g. actagardine, actagardine B, or deoxy-actagardine B) and diaminoalkane derivatised products.

| | | | | |
|---|---|---|---|---|
| Column: | Zorbax 5µ C18(2) 150 × 4.6 mm | | | |
| Mobile Phase A: | 30% Acetonitrile in 20 mM potassium phosphate buffer pH 7.0 | | | |
| Mobile Phase B: | 65% Acetonitrile in 20 mM potassium phosphate buffer pH 7.0 | | | |
| Flow rate: | 1 mL/min | | | |
| Gradient: | Time 0 min | 100% A | | 0% B |
| Time 10 min | 0% A | | 100% B | |
| Time 11 min | 0% A | | 100% B | |
| Time 11.2 min | 100% A | | 0% B | |
| Cycle time 15 min | | | | |
| Injection volume: | 10 µL | | | |
| Detection: | 210 nm | | | |

The crude reaction mixture was poured into 30% aqueous methanol and the resulting solution was loaded on to a Varian Bond Elut C18 column (30 g). The column was then washed sequentially with 50%, 60%, 70%, 80%, 90% aqueous methanol, with most of the desired material eluting in the 70% fraction (FIG. 6) Column chromatography on silica gel (eluent dichloromethane:ethanol:ammonia 10:8:1) gave material of >90% purity by U.V. at 210 nm. Yield 107 mg (50%). Mass calculated for $(M+2H)^{+2}$ 1015.5, found 1015.57. Calculated for $[M+H+Na]^{+2}$ 1026, found 1025.32

Samples were analysed by LC-MS using the conditions described in Table 2.

TABLE 2

LC/MS conditions for the analysis of lantibiotic (e.g. deoxy-actagardine B) and derivatised products.

| | |
|---|---|
| Column: | Zorbax 5µ C18(2) 150 × 4.6 mm |
| Mobile Phase A: | 10% acetonitrile, 0.1% formic acid |
| Mobile Phase B: | 90% acetonitrile, 0.1% formic acid |
| Flow rate: | 1 mL/min |

TABLE 2-continued

LC/MS conditions for the analysis of lantibiotic (e.g. deoxy-actagardine B) and derivatised products.

| | | | |
|---|---|---|---|
| Gradient: | Time 0 min | 100% A | 0% B |
| | Time 10 min | 0% A | 100% B |
| | Time 11 min | 0% A | 100% B |
| | Time 11.1 min | 100% A | 0% B |
| | Cycle time 15 min | | |
| Injection volume: | 20 µL | | |
| Mass Spectrometer parameters | | | |
| Ionisation | Electrospray +ve | | |
| Mass range | 250-1500 mu | | |
| Capillary voltage | 3.10 KV | | |
| Cone voltage | 40 V | | |
| Skimmer lens offset | 5 V | | |
| Ion energy | 1.4 V | | |

The compound of Example 1 after column chromatography was treated with 1.2 eq of N-methyl-D-glucamine in 50% aqueous methanol. Evaporation of the resultant solution affords the product as a white solid. The product thereof is referred to herein as Example 1a.

Example 2

Actagardine
(3,5-dichlorobenzylamine)monocarboxamide

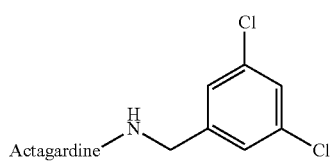

Actagardine (3,5-dichlorobenzylamine)monocarboxamide was prepared from actagardine and 3,5-dichlorobenzylamine according to the procedure described for Example 1. Yield 8%. Calculated for [M+2H]$^{+2}$ 1023.5, found 1023.7

Example 3

Deoxyactagardine B 19-[4-(4'-nitrophenyl)piperazine]monocarboxamide

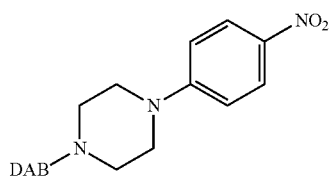

Deoxyactagardine B [4-(4'-nitrophenyl)piperazine]monocarboxamide was prepared from deoxyactagardine B and 4-nitrophenyl-piperazine utilising the procedure described for Example 1. Yield 73%. Calculated for [M+2H]$^{+2}$ 1031.5, found 1031.9

Example 4

Deoxyactagardine B 19-[4-(4'-chlorophenyl)piperazine]monocarboxamide

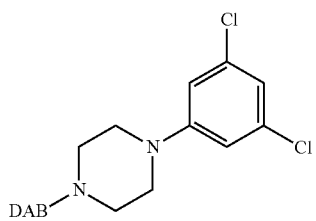

Deoxyactagardine B 19-[4-(4'-chlorophenyl)piperazine]monocarboxamide was prepared from deoxyactagardine B and 4-chlorophenyl-piperazine utilising the procedure described for Example 1. Yield 95%. Calculated for [M+2H]$^{+2}$ 1026.0, found 1026.2

Example 5

Deoxyactagardine B [2,4-dichlorobenzylamine]monocarboxamide

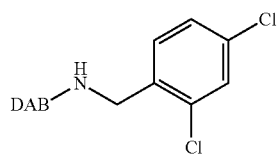

Deoxyactagardine B (2,4-dichlorobenzylamine)monocarboxamide was prepared from deoxyactagardine B and 2,4-dichlorobenzylamine utilising the procedure described for Example 1. Yield 86%. Calculated for [M+2H]$^{+2}$ 1015.5, found 1015.1

Example 6

Deoxyactagardine B [4-(3',5'-dichlorobenzyl)piperazine]monocarboxamide

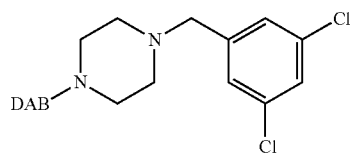

Deoxyactagardine B [4-(3',5'-dichlorobenzyl)piperazine]monocarboxamide was prepared from deoxyactagardine B and 4-(3',5'-dichlorobenzyl)piperazine utilising the procedure described for Example 1. Yield 80%. Calculated for [M+2H]$^{+2}$ 1050.0, found 1050.3

Example 7

Deoxyactagardine B [4-(2'-fluoro-4'-bromobenzyl)piperazine]monocarboxamide

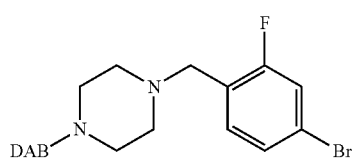

Deoxyactagardine B [4-(2'-fluoro-4'-bromobenzyl)piperazine]monocarboxamide was prepared from deoxyactagardine B and 4-(2'-fluoro-4'-bromobenzyl)piperazine utilising the procedure described for Example 1. Yield 83%. Mass calculated for (M+H2H)$^{+2}$ 1064.5, found 1063.7

Example 8

Deoxyactagardine B [4-(4'-nitrobenzyl)piperazine]monocarboxamide

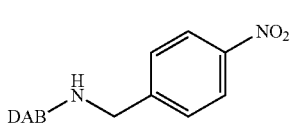

Deoxyactagardine B 19-[4-(4'-nitrobenzyl)piperazine]monocarboxamide was prepared from deoxyactagardine B and 4-(4'-nitrobenzyl)piperazine utilising the procedure

Example 9

Deoxyactagardine B [4-bromobenzylamine]monocarboxamide

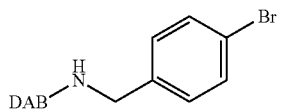

Deoxyactagardine B [4-bromobenzylamine]monocarboxamide was prepared from deoxyactagardine B and 4-bromobenzylamine utilising the procedure described for Example 1. Yield 92%. Mass calculated for $(M+2H)^{+2}$ 1021, found 1022.6

Example 10

Deoxyactagardine B [4-(3',4'-dichlorophenyl)piperazine]monocarboxamide

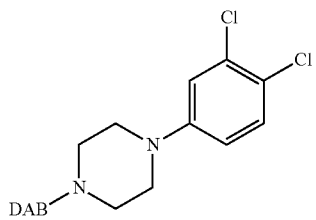

Deoxyactagardine B [4-(3',4'-dichlorophenyl)piperazine]monocarboxamide was prepared from deoxyactagardine B and 4-(3',4'-dichlorophenyl)piperazine utilising the procedure described for Example 1. Yield 33%. Calculated for $[M+2H]^{+2}$ 1043.0, found 1043.5

Example 11

Deoxyactagardine B [3-(3',5'-dichlorobenzylamino)-1-propylamine]monocarboxamide

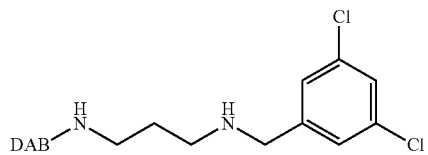

A suspension of sodium borohydride (0.26 g) in dichloromethane was treated with acetic acid (1.6 ml) and stirred for 15 minutes. A solution of N-Boc-1,3-diaminopropane (0.2 g) and 3,5-dichlorobenzaldehyde (0.61 g) in dichloromethane (10 mL) was added and the mixture was stirred at room temperature for 20 h. The mixture was then partitioned between aqueous sodium bicarbonate and ethyl acetate. The organic solution was evaporated and the residue purified by column chromatography on silica gel to yield 3-(3',5'-dichlorobenzylamino)-1N-(t-butoxycarbonyl)-propylamine as a white solid.

The purified product was dissolved in 90% trifluoroacetic acid (4 mL) and stirred for 3 h at room temperature. The trifluoroacetic acid was removed in vacuo and the residue partitioned between the mixture was then partitioned between aqueous sodium bicarbonate and ethyl acetate. The organic extracts were dried (MgSO$_4$) and evaporated to leave N-(3',5'-dichlorobenzyl)-1,3-diaminopropane as a white solid.

To a solution of deoxyactagardine B (1.0 g), N-(3',5'-dichlorobenzyl)-1,3-diaminopropane (0.34 g) and diisopropylethylamine (0.32 ml) in dry dimethylformamide (5 ml) a solution of benzotriazole-1-yl-oxy-tris-pyrrolidino-phosphonium hexafluorophosphate (PyBOP) (0.52 g) in dry dimethylformamide (2 mL) was added in portions until the reaction was complete as measured by analytical hplc (conditions as in Table 1). The coupling product was purified as described for the compound of Example 1. Yield 33%. Calculated for $[M+2H]^{+2}$ 1043.0, found 1043.49.

Example 12

Deoxyactagardine B [7-(3',5'-dichlorobenzylamino)-1-heptylamine]monocarboxamide

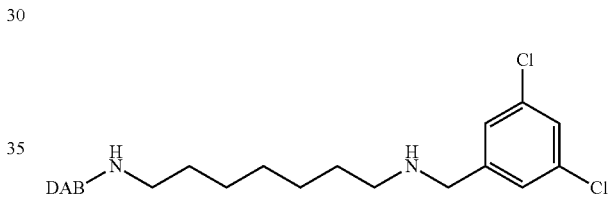

Was prepared from deoxyactagardine B, N-Boc-1,7-diaminoheptane and 3,5-dichlorobenzaldehyde as described for Example 11. Yield 35%. Calculated for $[M+2H]^{+2}$ 1072.0, found 1073.0

Example 13

Deoxyactagardine B [4-(2'-(3",5"-dichlorobenzylamino)ethyl)piperazine]monocarboxamide

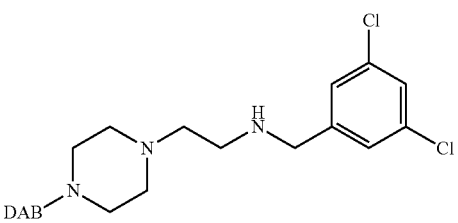

Was prepared from deoxyactagardine B, N-(2-aminoethyl)-piperazine and 3,5-dichlorobenzaldehyde as described for Example 11. Yield 15%. Calculated for $[M+2H]^{+2}$ 1071.5, found 1072.3

Example 14

Deoxyactagardine B
[1-(4-chlorophenyl)piperazine]monocarboxamide

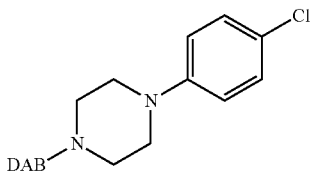

Deoxyactagardine B [1-(4-chlorophenyl)piperazine]monocarboxamide was prepared from deoxyactagardine B and 1-(4-chlorophenyl)piperazine utilising the procedure described for Example 1. Yield 21%. Calculated for [M+H]+ 2051, found 2052.8

Example 15

Deoxyactagardine B
(2,4-difluorobenzylamine)monocarboxamide

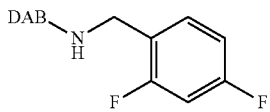

Deoxyactagardine B (2,4-difluorobenzylamine)monocarboxamide was prepared from deoxyactagardine B and 2,4-difluorobenzylamine utilising the procedure described for Example 1. Yield 31%. Calculated for [M+H]+2000.39, found 1999.5

Example 16

Deoxyactagardine B 19-[4-(2'-(3",5"-dinitrobenzamido)-ethyl)-piperazine]monocarboxamide

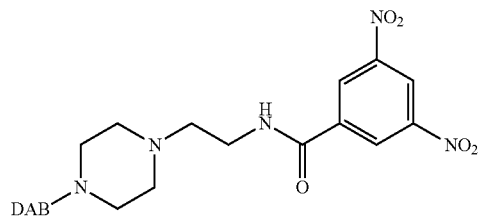

Deoxyactagardine B 19-[4-(2'-(3",5"-dinitrobenzamido)-ethyl)-piperazine]monocarboxamide was prepared from deoxyactagardine B and 4-(2'-(3",5"-dinitrobenzamido)-ethyl)-piperazine utilising the procedure described for Example 1. Yield 20%.

Example 17

V15F Actagardine
(3,5-dichlorobenzylamine)monocarboxamide

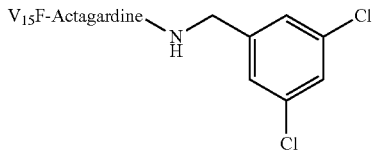

V15F Actagardine (3,5-dichlorobenzylamine)monocarboxamide was prepared from V15F Actagardine and 3,5-dichlorobenzylamine utilising the procedure described for Example 1. Yield 39%. Calculated for [M+Na H]$^{+2}$ 1058.5, found 1059. V15F actagardine is where valine 15 in the ring is replaced by phenylalanine.

Example 18

Deoxyactagardine B [3-(3',5'-dichlorobenzamido)propylamine]monocarboxamide

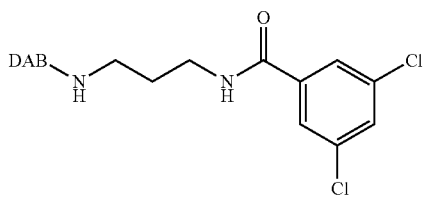

Deoxyactagardine B [3-(3',5'-dichlorobenzamido)-propylamine]monocarboxamide was prepared from deoxyactagardine B and 3-(3',5'-dichlorobenzamido)-propylamine utilising the procedure described for Example 1. Yield 61%. Calculated for [M+Na+H]$^{+2}$ 1062, found 1062

Example 19

Deoxyactagardine B [4-(3',5'-dichlorobenzylaminomethyl)benzyl]monocarboxamide

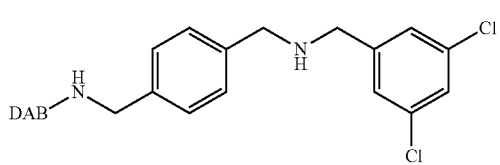

Deoxyactagardine B 19-[4-(3',5'-dichlorobenzylaminomethyl)-benzyl]monocarboxamide was prepared from deoxyactagardine B and 4-(3',5'-dichlorobenzylaminomethyl)-benzylamine utilising the procedure described for Example 1. Yield 37%. Calculated for [M+2H]$^{+2}$ 1075, found 1076.

Example 20

Deoxyactagardine B [3-(3'-(3",5"-dichlorobenzylamino)propylamino)propylamine]monocarboxamide

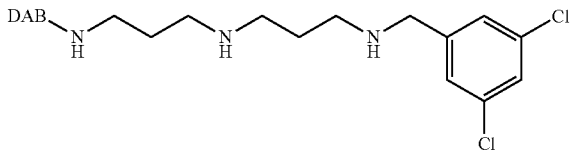

Deoxyactagardine B [3-(3'-(3",5"-dichlorobenzylamino)propylamino)propylamine]monocarboxamide was prepared from deoxyactagardine B and 3-(3'-(3",5"-dichlorobenzylamino)propylamino)propylamine utilising the procedure described for Example 1. Yield 22%. Calculated for [M+2H]$^{+2}$ 1072.5, found 1073

Example 21

Deoxyactagardine B (2,5-dichlorobenzylamine)monocarboxamide

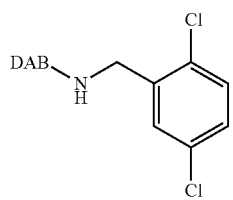

Deoxyactagardine B (2,5-dichlorobenzylamine)monocarboxamide was prepared from deoxyactagardine B and 2,5-dichlorobenzylamine utilising the procedure described for Example 1. Yield 57% Calculated for [M+Na+2H]$^{+2}$ 1026.5, found 1026.8

Example 22

Deoxyactagardine B (3,4-dichlorobenzylamine)monocarboxamide

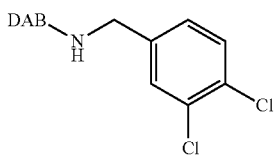

Deoxyactagardine B (3,4-dichlorobenzylamine)monocarboxamide was prepared from deoxyactagardine B and 3,4-dichlorobenzylamine utilising the procedure described for Example 1. Yield 41%. Calculated for [M+Na+H]$^{+2}$ 1026.5, found 1026.2

Example 23

Deoxyactagardine B (2-chlorobenzylamine)monocarboxamide

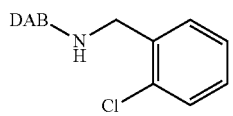

Deoxyactagardine B (2-chlorobenzylamine)monocarboxamide was prepared from deoxyactagardine B and 2-chlorobenzylamine utilising the procedure described for Example 1. Yield 50%. Calculated for [M+Na+H]$^{+2}$ 1009.5, found 1009.6

Example 24

Deoxyactagardine B (3-chlorobenzylamine)monocarboxamide

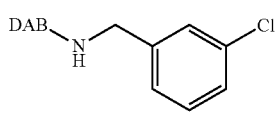

Deoxyactagardine B (3-chlorobenzylamine)monocarboxamide was prepared from deoxyactagardine B and 3-chlorobenzylamine utilising the procedure described for Example 1. Yield 62%. Calculated for [M+Na+H]$^{+2}$ 1009.5, found 1009.4

Example 25

Deoxyactagardine B (4-chlorobenzylamine)monocarboxamide

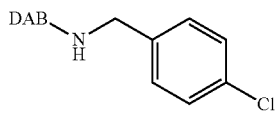

Deoxyactagardine B (4-chlorobenzylamine)monocarboxamide was prepared from deoxyactagardine B and 4-chlorobenzylamine utilising the procedure described for Example 1. Yield 40% Calculated for Calculated for [M+Na+H]$^{+2}$ 1009.5, found 1009.9

Example 26

Deoxyactagardine B (2,6-dichlorobenzylamine)monocarboxamide

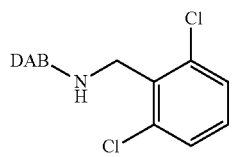

Deoxyactagardine B (2,6-dichlorobenzylamine)monocarboxamide was prepared from deoxyactagardine B and 2,6-dichlorobenzylamine utilising the procedure described for Example 1. Yield 57%. Calculated for [M+Na+H]$^{+2}$ 1026.5, found 1026.2

Example 27

Deoxyactagardine B [6-(2',4',6'-trichlorobenzenesulfonamido)hexylamine]monocarboxamide

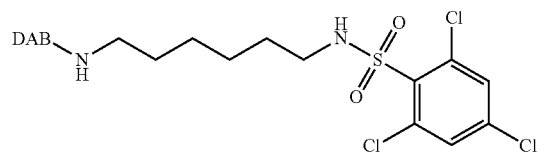

Deoxyactagardine B [6-(2',4',6'-trichlorobenzenesulfonamido)-hexylamine]monocarboxamide was prepared from deoxyactagardine B and 6-(2',4',6'-trichlorobenzenesulfonamido)-hexylamine utilising the procedure described for Example 1. Yield 73%. Calculated for [M+2H]$^{+2}$ 2213, found 2212.8

Example 28

Deoxyactagardine B [5-(3',5'-dichlorobenzylamino)-pentylamine]monocarboxamide

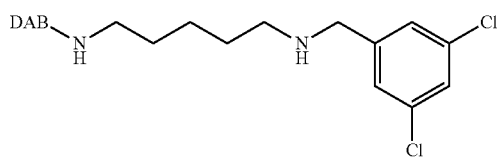

Deoxyactagardine B [5-(3',5'-dichlorobenzylamino)-pentylamine]monocarboxamide was prepared from deoxyactagardine B and 5-(3',5'-dichlorobenzylamino)-pentylamine utilising the procedure described for Example 1. Yield 36%. Calculated for [M+2H]$^{+2}$ 1058.0, found 1059.0

Example 29

Deoxyactagardine B [2-(3',5'-dichlorobenzylamino)ethylamine]monocarboxamide

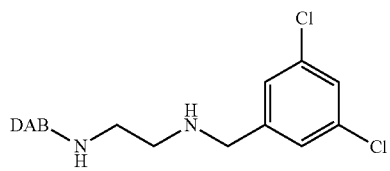

Deoxyactagardine B [2-(3',5'-dichlorobenzylamino)ethylamine]monocarboxamide was prepared from deoxyactagardine B and 2-(3',5'-dichlorobenzylamino)ethylamine utilising the procedure described for Example 1. Yield 51% Calculated for [M+2H]$^{+2}$ 1037.0, found 1038.0

Example 30

Deoxyactagardine B [6-(3',5'-dichlorobenzylamino)-hexylamine]monocarboxamide

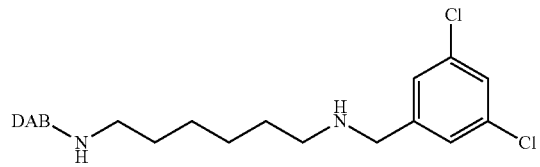

Deoxyactagardine B [6-(3',5'-dichlorobenzylamino)-hexylamine]monocarboxamide was prepared from deoxyactagardine B and 6-(3',5'-dichlorobenzylamino)-hexylamine utilising the procedure described for Example 1. Yield 51% Calculated for [M+2H]$^{+2}$ 1065.0, found 1065.8

Example 31

Deoxyactagardine B [8-(3',5'-dichlorobenzylamino)octylamine]monocarboxamide

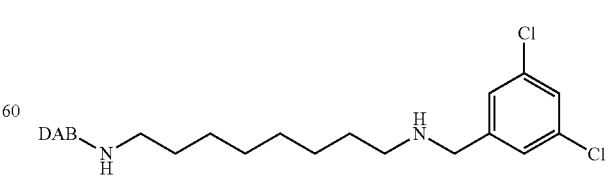

Deoxyactagardine B [8-(3',5'-dichlorobenzylamino)-octylamine]monocarboxamide was prepared from deoxyactagardine B and 8-(3',5'-dichlorobenzylamino)-octylamine utilising the procedure described for Example 1. Yield 63%. Calculated for $[M+2H]^{+2}$ 1079, found 1080.

Example 32

Deoxyactagardine B [3-(2'-aminomethyl-4'-(2",4"-dichlorophenyl)-furanyl)propylamine]monocarboxamide

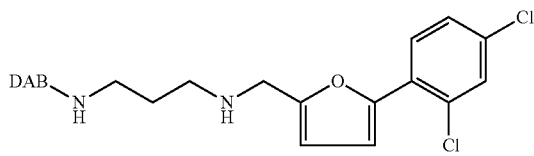

Deoxyactagardine B [3-(2'-aminomethyl-4'-(2",4"-dichlorophenyl)-furanyl)propylamine]monocarboxamide was prepared from deoxyactagardine B and 3-(2'-aminomethyl-4'-(2",4"-dichlorophenyl)-furanyl)propylamine utilising the procedure described for Example 1. Yield 11%. Calculated for $[M+2H]^{+2}$ 1077, found 1079.

Example 33

Deoxyactagardine B [3-(2'-aminomethyl-4'-(2"-nitro-4"-chlorophenyl)-furanyl)propylamine]monocarboxamide

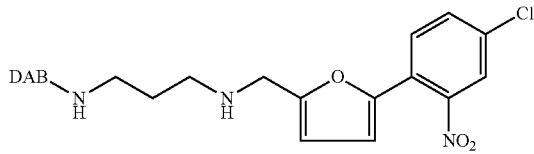

Deoxyactagardine B [3-(2'-aminomethyl-4'-(2"-nitro-4"-chlorophenyl)-furanyl)propylamine]monocarboxamide was prepared from deoxyactagardine B and [3-(2'-aminomethyl-4'-(2"-nitro-4"-phenyl)-furanyl)propylamine utilising the procedure described for Example 1. Yield 11%. Calculated for $[M+2H]^{+2}$ 1084, found 1083.5.

Example 34

Antibacterial activity of compounds of the invention

|  | Eg 1 MIC µg/mL | Eg 11 MIC µg/mL |
|---|---|---|
| Vancomycin resistant *Enterococci* |  |  |
| *E. faecium* 7662769 | 8 | 4-8 |
| *E. faecium* 7634337 | ≤4 | 8 |
| *E. faecium* 7865532 | ≤4 | 4-8 |
| *E. faecium* 9709024 | ≤4 | 4-8 |
| *E. faecium* 9710577 | 8 | 8 |
| *E. faecalis* GRL05031 | ≤4 | ≤4 |
| *E. faecalis* GRL05032 | ≤4 | ≤4 |
| *E. faecalis* GRL05033 | ≤4 | ≤4 |
| *E. faecalis* GRL05034 | ≤4 | ≤4 |
| *E. faecalis* GRL05035 | ≤4 | ≤4 |
| *E. faecalis* 9758512 | 8 | ≤4 |

-continued

|  | Eg 1 MIC µg/mL | Eg 11 MIC µg/mL |
|---|---|---|
| *E. faecium* 9704998 | ≤4 | 4-8 |
| *E. faecium* 7860190 | 4-8 | 4-8 |
| *S. pyogenes* |  |  |
| *S. pyogenes* 7755441 | ≤2 | ≤2 |
| *S. pyogenes* 7713283 | ≤2 | ≤2 |
| *S. pyogenes* 7865253 | ≤2 | ≤2 |
| *S. pyogenes* 7757080 | ≤2 | ≤2 |
| *S. pyogenes* 7755255 | ≤2 | ≤2 |
| *S. pyogenes* 7865844 | ≤2 | ≤2 |
| *S. pyogenes* GRL05045 | ≤2 | ≤2 |
| *S. pyogenes* GRL05046 | ≤2 | ≤2 |
| *S. pyogenes* 7865289 | ≤2 | ≤2 |
| *S. pyogenes* GRL05043 | ≤2 | ≤2 |
| *S. pyogenes* 7755584 | ≤2 | ≤2 |
| *S. pyogenes* GRL05042 | ≤2 | ≤2 |
| *S. pyogenes* GRL05041 | ≤2 | ≤2 |

|  | MIC in µg/mL against strain | |
|---|---|---|
| Compound/Example | *S. aureus* R33 (MRSA) | *S. aureus* SH1000 |
| Deoxyactgardine B | 8-16 | 8-16 |
| Actagardine | 8-16 | 8-16 |
| 1 | ≤4 | ≤4 |
| 2 | ≤4 | ≤4 |
| 3 | ≤4 | ≤4 |
| 4 | ≤4 | ≤4 |
| 5 | 8 | 8 |
| 6 | ≤4 | ≤4 |
| 7 | 8 | 8 |
| 8 | 8 | ≤4 |
| 9 | ≤4 | 8 |
| 10 | ≤4 | 8 |
| 11 | ≤4 | ≤4 |
| 12 | ≤4 | ≤4 |
| 13 | ≤4 | ≤4 |
| 14 | ≤4 | ≤4 |
| 15 | 8 | 8 |
| 16 | 8 | ≤4 |
| 17 | 8 | 16 |
| 18 | 8 | 16 |
| 19 | ≤4 | ≤4 |
| 20 | 8 | 8 |
| 21 | ≤4 | ≤4 |
| 22 | ≤4 | ≤4 |
| 23 | ≤4 | ≤4 |
| 24 | ≤4 | ≤4 |
| 25 | ≤4 | ≤4 |
| 26 | 8 | 8 |
| 27 | 8 | 8 |
| 28 | 8 | 4 |
| 29 | 16 | 8 |
| 30 | 8 | 4 |
| 31 | 16 | 8 |
| 32 | ≤4 | ≤4 |
| 33 | ≤4 | ≤4 |

| Strain | Isolate identification | Penicillin category | MIC (µg/mL) | |
|---|---|---|---|---|
|  |  |  | Example 1 | *Erythromycin* |
| *Streptococcus pneumonia* | QB37301 | Resistant | 2 | >32 |
|  | QB37302 | Resistant | 1 | >32 |
|  | QB37303 | Intermediate | 0.25 | ≤0.015 |
|  | QB37304 | Susceptible | 0.25 | 8 |
|  | QB37305 | Susceptible | 1 | 0.03-0.015 |
|  | QB37306 | Susceptible | 0.25-0.5 | ≤0.015 |
|  | QB37307 | Intermediate | 0.5-1 | ≤0.015 |

-continued

| Strain | Isolate identification | Penicillin category | MIC (μg/mL) Example 1 | Erythromycin |
|---|---|---|---|---|
| | QB37308 | Susceptible | 0.25-0.5 | ≤0.015 |
| | QB37309 | Resistant | 2 | 2 |
| | QB37310 | Resistant | 0.25 | >32 |
| | QB37311 | Resistant | 0.03 | >32 |
| | QB37312 | Intermediate | 0.5 | >32 |
| | QB37313 | Susceptible | 0.03 | >32 |
| | QB37314 | Resistant | 1 | >32 |
| | QB37315 | Susceptible | 0.25 | ≤0.015 |
| | QB37316 | Susceptible | 2 | ≤0.015 |
| | QB37317 | Susceptible | 0.25 | ≤0.015 |
| | QB37318 | Resistant | 0.25 | 4 |
| | QB37319 | Resistant | 1 | >32 |
| | QB37320 | Intermediate | 1 | 0.03-0.015 |

Susceptibility testing with the exception of *Streptococcus pneumoniae* was performed by two-fold serial dilutions in Mueller Hinton Broth supplemented with 50 μg/mL $Ca^{2+}$. Susceptibility testing of *S. pneumoniae* was performed by two-fold serial dilutions in Brain-Heart-Infusion Broth supplemented with 50 μg/mL $Ca^{2+}$.

Example 35

In vivo efficacy of compounds in a mouse bacteraemia model

Groups of 6 male CD-1 (Crl.) derived mice weighing 24±2 g were used. Mice were inoculated intraperitoneally (IP) with an $LD_{90-100}$ of *Staphylococcus aureus* methicillin resistant ATCC 33591 ($1.1 \times 10^7$ CFU/mouse) in 0.5 mL of BHI broth containing 5% mucin. The compound of example 1a and vancomycin were dissolved in 15% HPbetaCD/4.4% glucose/0.5 mM $KH_2PO_4$, pH 5.0 at doses of 1, 3, 5, 10 and 20 mg/Kg and were administered subcutaneously (SC) to test animals at 0, 2 and 24 hour(s) after bacteria challenge. The dosing volume was 5 mL/Kg. Mortality was recorded once daily for 7 days. The $ED_{50}$ for each compound was determined by nonlinear regression.

It was demonstrated that the compound of Example 1a at 3, 5, 10 and 20 mg/Kg×3, SC was associated with a significant antimicrobial effect against *S. aureus* (MR) in mice (at least 50% increase in survival rate) with an estimated $ED_{50}$ value of 1.07 mg/Kg).

Concurrently, vancomycin at 3, 5, 10 and 20 mg/Kg×3, SC exhibited significant antimicrobial effect against *S. aureus* (MR) in mice with an estimated $ED_{50}$ value of 3.0 mg/Kg. Survival data at doses of 3 mg/Kg are graphically summarised in FIG. 1.

Mice which received the compound of Example 1a at 3 mg/Kg had a 100% survival rate.

Example 36

Efficacy of compounds in a neutropaenic mouse thigh infection model

Figure 2:
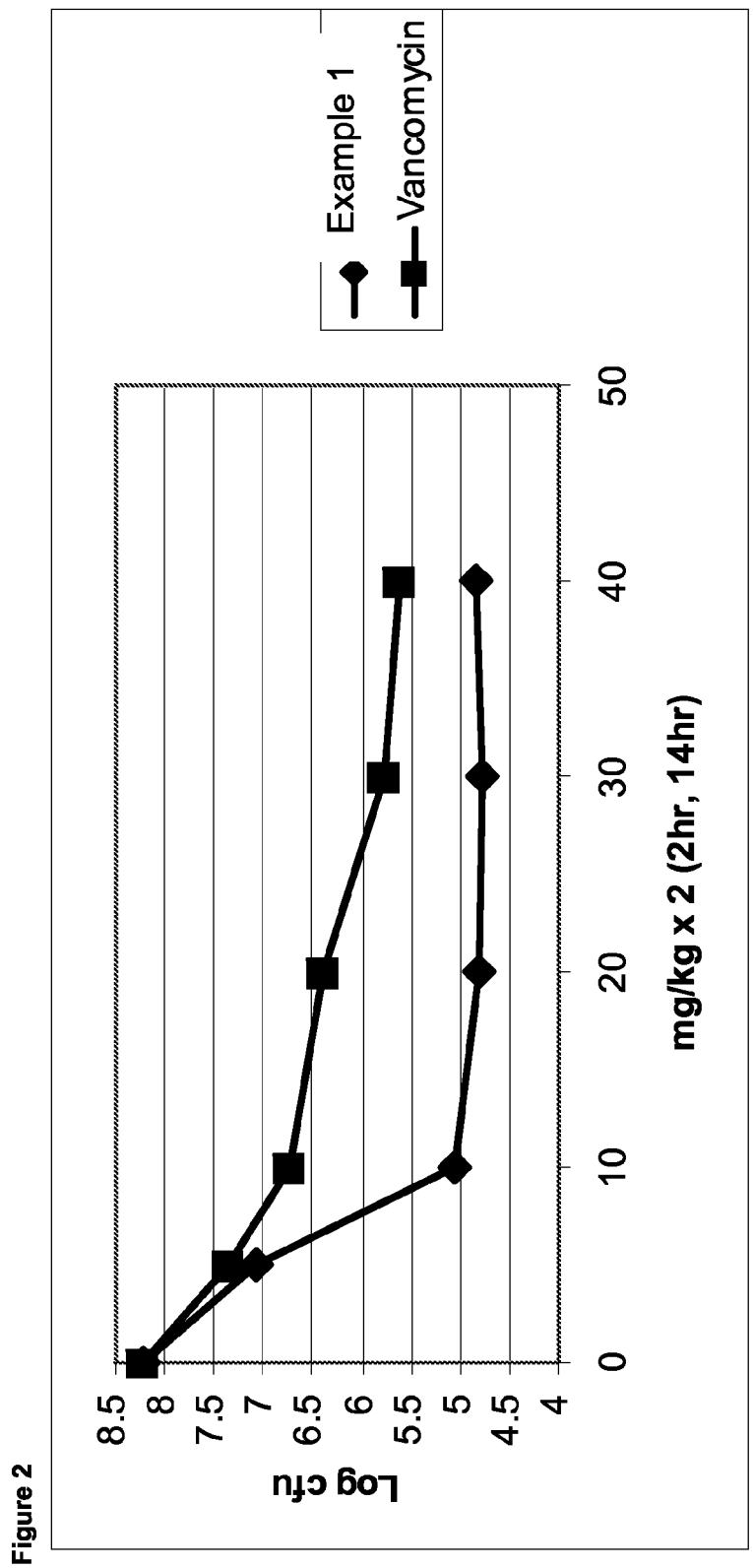
FIG. 2 shows the efficacy of intravenous administration of the compound of Example 1a and vancomycin, dosed at 5, 10, 20, 30, 40 mg/Kg after 2 hours and 14 hours with evaluation at 26 hours on the CFU/Kg in isolated homogenised thigh muscle of neutropaenic mice—(MRSA) *Staphylococcus aureus*, methicillin resistant (ATCC 33591).

In vivo efficacy of compounds of the present invention in the treatment of bacterial tissue infections was evaluated using a neutropaenic mouse thigh model. See FIG. 2. Groups of 6 male ICR mice weighing 24±2 g were used. Test animals were immunosuppressed by 2 intraperitoneal injections of cyclophosphamide, the first at 150 mg/Kg 4 days before infection (day-4) and the second at 100 mg/Kg 1 day before infection (day-1). On day 0, individual animals were inoculated intramuscularly (IM) into the right thigh of test animals with $1.15 \times 10^5$ CFU/mouse of Methicillin Resistant *Staphylococcus aureus* (MRSA, ATCC 33591) suspended in 100 μL of sterile PBS, pH 7.4. Vehicle and test substances were administered intravenously (IV) at a dose volume of 8 mL/Kg, 2 and 14 hours after thigh infection. Example 1a (Compound I) and vancomycin were dissolved in 15% hydroxypropyl-β-cyclodextrin/4.4% glucose/1 mM potassium phosphate buffer, pH 7.0 and administered at doses of 5, 10, 20, 30 and 40 mg/Kg. At 26 hours after inoculation, muscle of the right thigh of each test mouse was harvested. From an additional group with no treatment, muscle of the right thigh was harvested at 2 hours after inoculation for the basal CFU determination. The removed muscle tissues were then homogenized in 3-4 mL of PBS, pH 7.4 with a ceramic mortar. Homogenates of 0.1 mL were used for serial 10-fold dilutions and plated on Mueller Hinton broth in 1.5% Bacto agar for CFU determination.

It was demonstrated that compound of Example 1a dosed IV at 5, 10, 20 30 and 40 mg/Kg×2, was associated with a significant antimicrobial effect, resulting in a >1000-fold reduction in CFU/g at 10 mg/kg and above. Concurrently, vancomycin also exhibited a significant antimicrobial effect with reductions of CFU/g of >100 fold at 30 mg/kg and above, whilst not attaining the >1000-fold reduction observed for Example 1a. Results are graphically represented in FIG. 2. The label Example 1 in FIG. 2 refers to compound of Example 1a.

Example 37

In vivo plasma half-life of compounds of the present invention in mice

Figure 3:
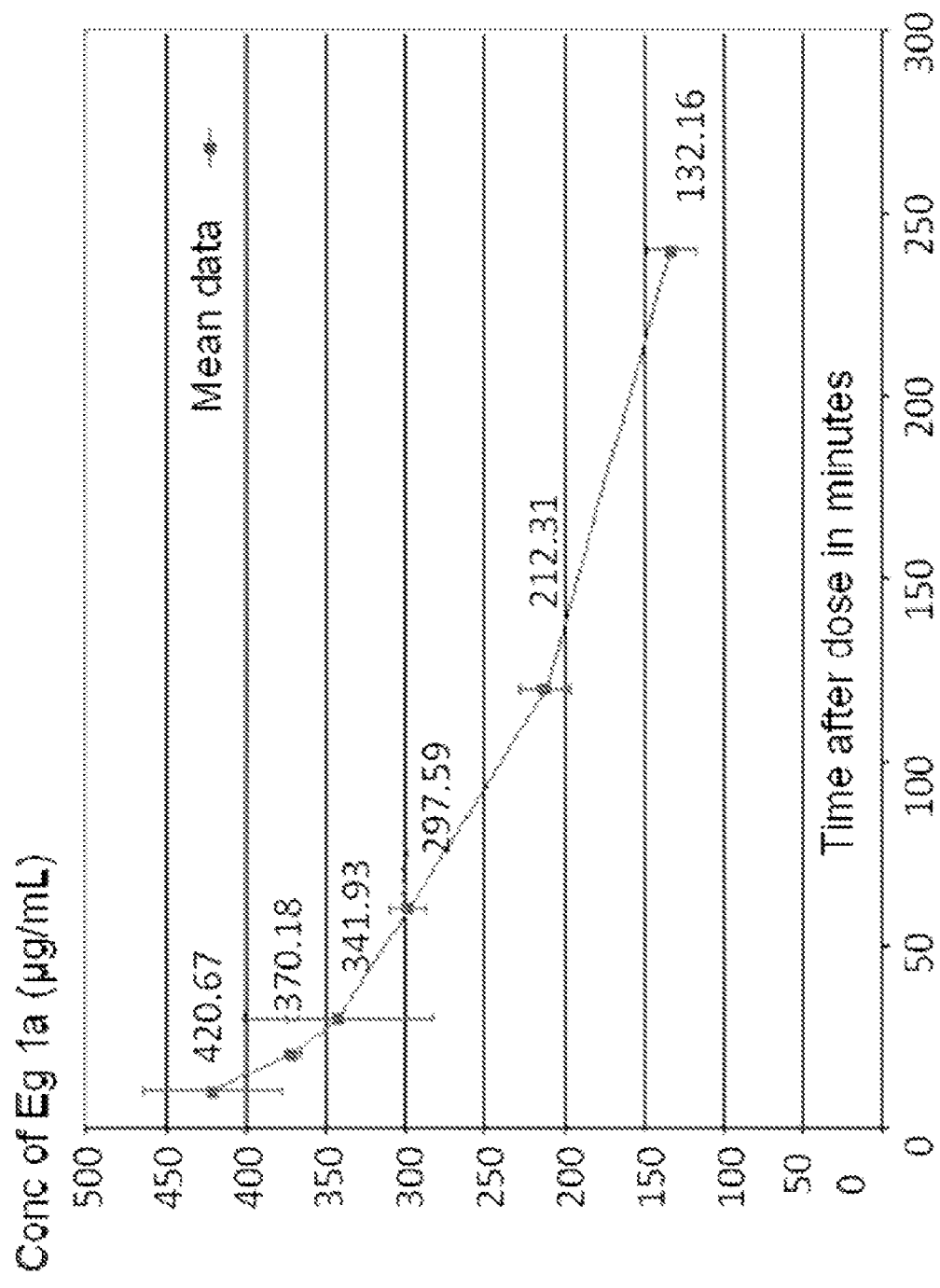
FIG. 3 shows a determination of plasma half life of the compound of Example 1a in the mouse. After i.v. dosing in male CD-1 mice the concentration of compound of Example 1a in blood plasma (mg/mL) was determined after 10, 20, 30, 60, 120 and 240 mins.

The in vivo half-life of Example 1a in mice was determined by measurement of its plasma concentrations at various time points following IV dosing. 18 male CD-1 mice aged 7-9 weeks were dosed IV with a 9.3 mL/Kg dose of a 3.2 mg/mL solution of Example 1a in 15% hydroxyl-propyl-β-cyclodextrin/4.4% glucose/1 mM potassium phosphate (pH=7.6). Plasma samples were obtained at 10, 20, 30, 60, 120 and 240 min post-dose, sampling from 3 animals at each time point. Concentrations of Example 1a in plasma were determined by LC-MS quantification. The data, summarised in FIG. 3, show that Example 1a has a plasma half-life of approximately 2 h in the mouse.

The invention claimed is:
1. A compound of formula (IV):

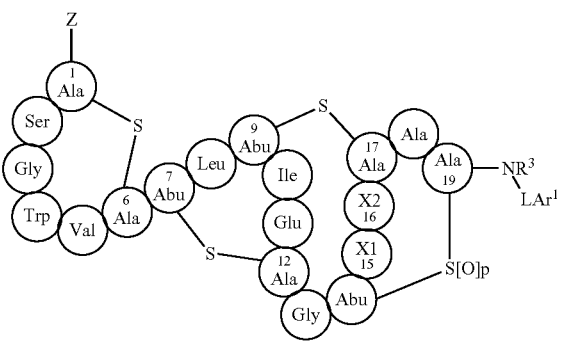

(IV)

wherein:
  X1 and X2 are Leu and Val, respectively or Val and Ile, respectively;
  $R^3$ is H or $C_{1-6}$ alkyl;
  L is a straight or branched $C_{0-15}$ alkyl chain wherein optionally one or more carbons are replaced by a heteroatom independently selected from the group consisting of N, O and S, wherein said chain is optionally substituted by one or more oxo or nitro groups with the proviso that a heteroatom is not bonded directly to the N of the group —$NR^3$;
  $Ar^1$ is phenyl substituted by one or two $NO_2$ groups, one to five halogen groups, one or two $C_{1-3}$ haloalkyl groups or a combination thereof;
  Z is selected from the group consisting of H, $C_{1-6}$ alkyl and an amino acid residue; and
  p is 0 or 1,
or a pharmaceutically acceptable salt thereof.

2. The compound according to claim 1, wherein Z is H or Ala.

3. The compound according to claim 2, wherein Z is H.

4. The compound according to claim 1, wherein $Ar^1$ is phenyl substituted by one or two $NO_2$ groups, one to five halogen groups or a combination thereof.

5. The compound according to claim 1, wherein $Ar^1$ is di-nitrophenyl or di-halophenyl.

6. The compound according to claim 5, wherein $Ar^1$ is selected from the group consisting of 3,5-di-chlorophenyl, 3,4-di-chlorophenyl, 2,4-di-chlorophenyl, 3,5-di-fluorophenyl, 3,4-di-fluorophenyl and 2,4-di-fluorophenyl.

7. The compound according to claim 5, wherein $Ar^1$ is selected from the group consisting of 3,5-di-nitrophenyl, 3,4-di-nitrophenyl and 2,4-di-nitrophenyl.

8. The compound according to claim 1, wherein L is $C_0$.

9. The compound according to claim 1, wherein L is a straight or branched $C_{1-9}$ alkyl chain wherein optionally one or more carbon(s) is/are replaced by a heteroatom selected from the group consisting of O, N and S.

10. The compound according to claim 9, wherein L is a straight alkyl chain.

11. The compound according to claim 10, wherein L is $CH_2$.

12. The compound according to claim 1, wherein L is —$(CH_2)_n NH(CH_2)_j$, i is an integer from 1 to 12, and j is 0 or 1.

13. The compound according to claim 12 wherein L is selected from the group consisting of —$(CH_2)_2 NHCH_2$—, —$(CH_2)_3 NHCH_2$—, —$(CH_2)_4 NHCH_2$—, —$(CH_2)_5 NHCH_2$—, —$(CH_2)_6 NHCH_2$—, —$(CH_2)_7 NHCH_2$— and —$(CH_2)_8 NHCH_2$—.

14. The compound according to claim 1 wherein L is a straight $C_{1-15}$ alkyl chain wherein optionally one or two carbons are replaced by a heteroatom independently selected from the group consisting of N, O and S, wherein said chain is optionally substituted by one or two oxo groups.

15. The compound according to claim 14, wherein L is selected from the group consisting of —$(CH_2)_3 NHCO$—, —$(CH_2)_3 NH(CH_2)_3 NHCH_2$— and —$(CH_2)_7 NHSO_2$—.

16. The compound according to claim 1 wherein $R^3$ is H.

17. A The compound according to claim 1 wherein X1 and X2 are Leu and Val, respectively.

18. The compound according to claim 1 wherein X1 and X2 are Val and Ile, respectively.

19. A compound selected from the group consisting of:
  Deoxyactagardine B (3,5-dichlorobenzylamine)monocarboxamide;
  Actagardine (3,5-dichlorobenzylamine)monocarboxamide;
  Deoxyactagardine B [2,4-dichlorobenzylamine]monocarboxamide;
  Deoxyactagardine B [4-bromobenzylamine]monocarboxamide;
  Deoxyactagardine B [3-(3',5'-dichlorobenzylamino)-1-propylamine]monocarboxamide;
  Deoxyactagardine B [7-(3',5'-dichlorobenzylamino)-1-heptylamine]monocarboxamide;
  Deoxyactagardine B (2,4-difluorobenzylamine)monocarboxamide;
  V15F Actagardine (3,5-dichlorobenzylamine)monocarboxamide;
  Deoxyactagardine B [3-(3',5'-dichlorobenzamido)-propylamine]monocarboxamide;
  Deoxyactagardine B [3-(3'-(3'',5''-dichlorobenzylamino)propylamino)propylamine]monocarboxamide;
  Deoxyactagardine B (2,5-dichlorobenzylamine)monocarboxamide;
  Deoxyactagardine B (3,4-dichlorobenzylamine)monocarboxamide;
  Deoxyactagardine B (2-chlorobenzylamine)monocarboxamide;
  Deoxyactagardine B (3-chlorobenzylamine)monocarboxamide;
  Deoxyactagardine B (4-chlorobenzylamine)monocarboxamide;
  Deoxyactagardine B (2,6-dichlorobenzylamine)monocarboxamide;
  Deoxyactagardine B [6-(2',4',6'-trichlorobenzenesulfonamido)-hexylamine]monocarboxamide;
  Deoxyactagardine B [5-(3',5'-dichlorobenzylamino)-pentylamine]monocarboxamide;
  Deoxyactagardine B [2-(3',5'-dichlorobenzylamino)ethylamine]monocarboxamide;
  Deoxyactagardine B [6-(3',5'-dichlorobenzylamino)-hexylamine]monocarboxamide
  Deoxyactagardine B [8-(3',5'-dichlorobenzylamino)-octylamine]monocarboxamide; and
pharmaceutically acceptable salts thereof.

20. A composition comprising a compound according to claim 1 and a pharmaceutically acceptable excipient.

21. A method of treatment of a *Staphylococcus aureus* bacterial infection comprising administering to a subject in need thereof an effective amount of the compound according to claim 1.

22. The method of treatment of a *Staphylococcus aureus* bacterial infection according to claim 21 wherein said infection is a methicillin resistant *Staphylococcus aureus*.

23. The compound according to claim 1, wherein L is a straight or branched $C_{0-15}$ alkyl chain wherein said chain is optionally substituted by one or more oxo or nitro groups with the proviso that a heteroatom is not bonded directly to the N of the group —$NR^3$.

24. The compound according to claim 1 which is Deoxyactagardine B (3,5-dichlorobenzylamine)monocarboxamide or a pharmaceutically acceptable salt thereof.

25. A method of treatment of a *Staphylococcus aureus* bacterial infection comprising administering to a subject in need thereof an effective amount of the compound according to claim 19.

26. The method of treatment of a *Staphylococcus aureus* bacterial infection according to claim 25 wherein said infection is a methicillin resistant *Staphylococcus aureus*.

* * * * *